US008567393B2

(12) United States Patent
Hickle et al.

(10) Patent No.: US 8,567,393 B2
(45) Date of Patent: Oct. 29, 2013

(54) USER INTERFACE FOR SEDATION AND ANALGESIA DELIVERY SYSTEMS AND METHODS

(75) Inventors: Randall S. Hickle, Lubbock, TX (US); Mica R. Endsley, Marietta, GA (US)

(73) Assignee: Scott Laboratories, Inc, Lubbock, TX (US)

(*) Notice: Subject to any disclaimer, the term of this patent is extended or adjusted under 35 U.S.C. 154(b) by 1401 days.

(21) Appl. No.: 10/285,689

(22) Filed: Nov. 1, 2002

(65) Prior Publication Data

US 2003/0135087 A1    Jul. 17, 2003

Related U.S. Application Data

(60) Provisional application No. 60/330,853, filed on Nov. 1, 2001.

(51) Int. Cl.
*A61M 15/00* (2006.01)
*A61M 16/00* (2006.01)

(52) U.S. Cl.
USPC ............ 128/203.14; 128/203.12; 128/204.18; 128/204.23; 128/200.24

(58) Field of Classification Search
USPC ............. 128/200.24, 203.12, 203.14, 204.21, 128/204.23, DIG. 13; 600/300, 301; 604/65, 604/66, 67, 23, 26, 155, 503
See application file for complete search history.

(56) References Cited

U.S. PATENT DOCUMENTS

| | | | |
|---|---|---|---|
| 4,308,866 A | 1/1982 | Jelliffe et al. .................. 128/214 |
| 4,509,133 A | 4/1985 | Monbaron et al. .......... 364/513.5 |
| 4,551,133 A | 11/1985 | Zegers de Beyl et al. |
| 4,634,426 A | 1/1987 | Kamen ............................ 604/65 |
| 4,638,422 A | 1/1987 | Rees ............................... 364/200 |
| 4,741,732 A * | 5/1988 | Crankshaw et al. .......... 604/503 |
| 5,183,038 A | 2/1993 | Hoffman et al. ......... 128/204.21 |
| 5,231,981 A | 8/1993 | Schreiber et al. ............. 128/205 |
| 5,258,906 A | 11/1993 | Kroll et al. ..................... 364/401 |
| 5,262,944 A | 11/1993 | Weisner et al. |
| 5,286,252 A | 2/1994 | Tuttle et al. ...................... 604/20 |
| 5,331,549 A | 7/1994 | Crawford, Jr. ........... 364/413.02 |
| 5,432,618 A | 7/1995 | Monnot et al. ................ 358/435 |
| 5,713,856 A | 2/1998 | Eggers et al. |

(Continued)

FOREIGN PATENT DOCUMENTS

| | | |
|---|---|---|
| EP | 0911052 A2 | 4/1999 |
| WO | WO 98/10701 | 3/1998 |
| WO | WO 99/62403 | * 12/1999 |
| WO | WO 01/24690 | 4/2001 |

OTHER PUBLICATIONS

International Search Report dated May 7, 2003, for Application No. PCT/US02/35091.

*Primary Examiner* — Annette Dixon
(74) *Attorney, Agent, or Firm* — Dorsey L Baker

(57) ABSTRACT

The present invention comprises a user interface for systems and methods for sedation and analgesia delivery. The user interface receives input from a user of a sedation and analgesia delivery system and relays information regarding the system, the administration of sedation and analgesia, physiological conditions to the user in a context sensitive manner. The information relayed may be displayed to the user on a touch sensitive screen or multi-layer display device. The display may be segregated geographically or may be color coded on the display device where the geographic location and/or color of the displayed information relates further information to the user.

36 Claims, 32 Drawing Sheets

(56) References Cited

U.S. PATENT DOCUMENTS

| | | | |
|---|---|---|---|
| 5,718,223 A * | 2/1998 | Protas et al. | 128/204.21 |
| 5,730,140 A | 3/1998 | Fitch | 128/701 |
| 5,733,259 A | 3/1998 | Valcke et al. | 604/66 |
| 5,795,301 A * | 8/1998 | Yasukawa et al. | 600/500 |
| 5,795,327 A | 8/1998 | Wilson et al. | |
| 5,957,885 A | 9/1999 | Bollish et al. | |
| 6,024,089 A * | 2/2000 | Wallace et al. | 128/204.21 |
| 6,146,523 A | 11/2000 | Kenley et al. | 210/143 |
| 6,302,844 B1 | 10/2001 | Walker et al. | |
| 6,305,372 B1 | 10/2001 | Servidio | |
| 6,305,373 B1 | 10/2001 | Wallace et al. | 128/204.21 |
| 6,328,708 B1 * | 12/2001 | Georgieff | 604/26 |
| 6,511,453 B2 * | 1/2003 | Georgieff | 604/26 |
| 6,638,218 B2 * | 10/2003 | Bulat | 600/300 |
| 6,757,558 B2 * | 6/2004 | Lange et al. | 600/544 |
| 6,807,965 B1 * | 10/2004 | Hickle | 128/204.23 |
| 7,081,095 B2 * | 7/2006 | Lynn et al. | 600/538 |
| 7,089,927 B2 * | 8/2006 | John et al. | 128/200.24 |
| 7,201,734 B2 * | 4/2007 | Hickle | 604/67 |
| 7,606,723 B2 * | 10/2009 | Mayaud | 705/2 |
| 7,776,031 B2 * | 8/2010 | Hartlaub et al. | 604/891.1 |

* cited by examiner

USER INTERFACE FOR SEDATION AND ANALGESIA DELIVERY SYSTEMS AND METHODS

This application claims priority under 35 U.S.C. §119(e) to U.S. patent application Ser. No. 60/330,853, filed Nov. 1, 2001 and incorporated herein by reference in its entirety.

FIELD OF THE INVENTION

The present invention relates generally to the field of control of a medical device and the field of enhancing the interactions within a patient-clinician-machine system where the clinician or clinicians may be multi-tasked. More particularly, the present invention relates to a user interface and control method for a medical device such as a sedation and analgesia delivery system.

BACKGROUND OF THE INVENTION

Designing user interfaces (UIs) for clinicians is an especially difficult task because many clinicians may not have the time or patience to sit through comprehensive in-service sessions. One viewpoint of some clinicians is that if they have to read a manual to operate a medical device, then the designer of that device has failed, because in some urgent circumstances, they may be required to operate devices for which no manual is readily available, on which they have not been fully trained, or when they have not recently used the device to maintain proficiency. Many medical devices fail this pragmatic, real-world definition of intuitiveness and usability. Given that poor usability can affect the eventual outcome of a clinical procedure, a well-designed user-interface that anticipates the needs of clinicians is essential.

With the advent of inexpensive microprocessors, the flexibility and power of UIs programmed in software has opened the possibility of designing UIs that implement more commands and provide more options and operational modes to the user. However, with the interfaces of certain existing devices, these commands may be hidden behind many hierarchical levels of sub-menus and may not be immediately or intuitively apparent to the user. In other instances, a set of commands may not be logically grouped from a clinical point of view on the keypad or in the logical menu structure such that the user may get lost navigating through the multiple buttons and sub-menu options. Similarly, multiple operational modes may confuse the user who may lose track of the operational mode currently in effect. For example, a physiological monitor inadvertently running in a simulation mode while connected to a real patient could confuse the user and represent a hazard if the data being displayed by the monitor was simulated data rather than the data from the patient connected to the monitor.

Touch screen input devices deliver flexibility to the UI designer, including the ability to implement an essentially infinite number of touch screen buttons or data entry boxes as well as last minute additions in software, without any need to add new hard keys or input devices. Thus, devices controlled by touch screens tend to have a reduced number of associated hard keys. The art of user interface design involves the careful balance of competing factors. For example, increased dependence on touch screen keys may lead to more hierarchical levels of sub-menus because it is generally not an option to show all the keys on one screen of limited size. However, having fewer hard keys could also mean that the medical device is dependent on touch screen keys and if the touch screen malfunctions, the medical device might lock up with the user no longer able to control system operation.

In yet other instances with existing medical devices, different physiological monitors may be stand-alone units that do not communicate with each other. The stand-alone monitors may be placed at different locations on different machines at different sites, such that a clinician practicing at multiple office based surgery locations, may have to look in different spots in each facility to inspect, for example, the electrocardiogram—a less than desirable situation. Considering the fact that multiple physiological parameters should be monitored (e.g., electrocardiogram, pulse oximetry data, noninvasive blood pressure, and capnometry readings), a clinician's ability to even find the available data, much less, to be able to cognitively integrate and analyze the relevant information on a real-time basis, can be severely limited. Furthermore, using the example of an anesthesia machine, a delivery subsystem's monitored machine parameter (e.g., inspired fraction of oxygen set by the $O_2$ and $N_2O$ ball-in-tube rotameter settings) may be physically separate from the corresponding monitored physiological parameter, arterial oxygen saturation, $SpO_2$. As an example, a monitored $SpO_2$ value should be interpreted in the context of the delivered inspired fraction of oxygen ($FiO_2$). Thus, separation of the $FiO_2$ setting (machine parameter) and $SpO_2$ display (related physiology parameter) and more generally separation of the therapy and corresponding monitored parameter(s) on a medical device are undesirable.

A UI may have a vital function as a window into the inner workings of a medical device to promote transparency of operation as well as to provide feedback that a user request has been performed. As an example of lack of transparency, in many existing patient monitoring devices, outdated data that is intermittently captured continues to be displayed even when the monitor has been turned off or placed in a standby mode. If the user has forgotten to turn the monitor back on after turning it off, he might be misled into thinking that the UI is displaying current physiologic data that is relevant for critical diagnostic and therapeutic decisions.

A properly designed UI should enhance the interactions within the clinician-machine-patient system. To lighten the cognitive workload or "data overload" of the user, instead of presenting raw data, the UI should present data that has already been processed into meaningful information that can be assimilated at a glance, thus providing timely decision support to the user.

User error can be prevented by clear and unambiguous controls and input devices. However other failure modes exist in current UI designs. For example, default settings can be the cause of mishaps as demonstrated by infusion pumps. When users mistakenly accepted the default concentration that was actually weaker than the actual drug concentration, drug overdose and death resulted. Confusion between units may also be the cause of error especially in situations where weight may be used to calculate drug infusion rates.

A UI should compensate for user forgetfulness, incorrect entry of data and lack of judgment as well as reducing memory load. In some current UIs, the user has to search the environment or the display of a device to identify what parameter is alarming, sometimes amid a cacophony of irritating alarms as well as determine which alarm is of highest priority, in the event of multiple alarms. Alarms on current UI designs sometimes generate alarms out of context. For example, alarms may sound when there is no patient connected to a medical device or at the end of the procedure when the patient is being disconnected from the device, perfect examples of alarms becoming a nuisance by telling the user something that is already known.

SUMMARY OF THE INVENTION

The present invention comprises a user interface for a sedation and analgesia delivery system, which enables a clinician who may or may not have experience with sedation and analgesia to easily and safely operate the system. The user interface consists of an interactive device such as a touch screen capable of displaying several different windows, some of which may be context sensitive, for exhibiting information about or interacting with the processes involved in a sedation and analgesia procedure and a separate keypad consisting of several buttons for activating or deactivating the major functionalities of the system independently of what is displayed on the touch screen. The display may also be a multi-layer display that facilitates high data densities such as those available from Deep Video Imaging.

The display of the UI places both data from patient monitors (e.g., heart rate, blood pressure, $SpO_2$, $ETCO_2$, and automated responsiveness testing ("ART")) and therapy data, i.e. information relating to drug and gas delivery, on a single screen, and this information is grouped to provide a meaningful cognitive framework for the user. For example, the monitored physiological parameters that provide the basis for understanding the cardiovascular/hemodynamic system are grouped in a single cluster, band, or on a single line. Similarly, information is grouped together to facilitate the user's mental model for analyzing oxygenation status, ventilatory status, and drug effect. The data is consistently updated throughout a procedure. In situations where it facilitates the mental model, current data for patient parameters are displayed both as a numerical value and as a graphical waveform. Historical data is also presented for user reference and comparison as well as detecting trends. The historical data provide information on amount and rate of change in heart rate, $SpO_2$, and $EtCO_2$, allowing clinicians arriving to help in an emergency or who or have been concentrating on surgical or other procedures to quickly assess the state of the patient at a glance.

The UI displays patient data in such a way on the geography of the touch screen that the user may easily make comparisons between the data reported from various sources. The user need not, then, look around a room full of instruments to make correlations or cross-validations between different data. Furthermore, the UI makes use of geographic as well as color encoding of information while also presenting both therapy controls and monitoring data on the same UI. For example, the system integrates the display of physiological data (e.g., heart rate, $SpO_2$, ECG, $CO_2$, etc.) with the display of drug levels based on pharmacokinetic calculations along a consistent timeline, thereby allowing the user to cross-correlate these parameters.

The UI allows for easy management and presentation of patient state alarms and system advisories. The display of the UI comprises a dedicated portion in which all current alarms and advisories are displayed according to their priority. The user need only look to one centralized location on a screen, therefore, to be abreast of all active alerts. The UI also provides redundant audio alerts for the alarms and advisories, which may be muted by the user for limited amounts of time. The user is presented with the remaining time left in a muted alarm but must take proactive steps to keep the audio alerts at bay to ensure that they are not forgotten.

During the set-up and administration of a sedation and analgesia procedure, when the user changes critical settings, the UI prompts the user to confirm his actions to reduce the likelihood of entry error. The user is presented with lists of ramifications of certain actions called for and is reminded to check that certain requisite predecessor conditions for the safety of sedation and analgesia have been satisfied before the system will administer drugs to a patient.

The system will warn the user via the UI if he takes certain actions that may be harmful to a patient, such as entering a potentially toxic dose of drug, entering inconsistent patient data, or starting sedation and analgesia without first satisfying requisite predecessor conditions and it will not allow sedation and analgesia to proceed. However, the design of the system also adheres to a "clinician knows best" philosophy. In other words, rather than trying to have the software anticipate every possible combination and permutation of conditions, the design acknowledges that not all possible clinical situations can be anticipated ahead of time and that the clinician taking care of the patient will, when given the appropriate data, make better decisions than a pre-defined system algorithm.

Time and labor intensive tasks like titrating drugs to effect during sedation and analgesia are partially automated by the judicious use of clinical heuristics and a drug state model that may be based, among others, on pharmacokinetic models and target controlled infusion of intravenous drugs. Only actions that have a high certainty of producing safe effects, like turning off drug infusion, are automated. Target controlled infusion (TCI) is also one of the ways of enhancing the user interface because instead of the user having to calculate the desired infusion rate profile over time, which would be very difficult to do as well as tedious and time-consuming to implement, the user interface in combination with the TCI algorithm, provides a user friendly way and much less time- and labor-intensive way to titrate the drugs to effect during sedation and analgesia.

Target controlled infusion and clinical heuristics are combined in a drug state model. The drug state model is also tightly integrated with the UI, the ART monitor and the drug delivery device of the sedation and analgesia delivery system to reduce the time and labor required to prevent the patient from inadvertently slipping into unconsciousness.

Some clinicians may be skeptical of a computer system controlling the delivery of potent drugs without human oversight. The UI supports a system design that provides the benefits of computer control, via clinical heuristics, such as reducing the time and labor intensive repetitive tasks such as titrating drugs to effect, while still supporting appropriate human oversight.

Conversely, a clinical heuristics algorithm that is overly conservative and safety-biased may interfere with the clinical course of a procedure, preventing the user from performing certain actions, like purposely giving an amount of drug that would cause unconsciousness in a non-stimulated patient, in anticipation of an imminent painful procedure. The UI anticipates such clinical situations by allowing the clinician to override the safety-biased heuristics and algorithms, after providing messages to the user to verify that she or he really wants to do this as well as explaining the consequences of the proposed action, in some instances.

The UI also presents constant notification of any changes made to system settings so that all potential users of the system may be aware that certain defaults have been abandoned. In many cases the user's knowledge of the current state of the system or of the expected achievements of the system's functions is reinforced by the UI's display of redundant icons and text characteristic of the same information.

Much of the time consuming aspects of delivering sedation and analgesia or anesthesia and titrating drugs to effect is automated using clinical heuristics and drug state models programmed into the control software. The UI is designed to support a clinical heuristics algorithm and target controlled infusion while allowing the user to override the pre-programmed heuristics so that the user is not locked out from using the medical device to its full potential.

DETAILED DESCRIPTION OF THE INVENTION

A user interface (UI) is described herein that may be functionally integrated with a sedation and analgesia delivery system. An example of such a sedation and analgesia delivery system is described in U.S. patent application Ser. No. 09/324,759, filed Jun. 3, 1999 and incorporated herein by reference in its entirety.

The sedation and analgesia system of application Ser. No. 09/324,759 includes a patient health monitor device adapted so as to be coupled to a patient and generate a signal reflecting at least one physiological condition of the patient, a drug delivery controller supplying one or more drugs to the patient, a memory device storing a safety data set reflecting safe and undesirable parameters of at least one monitored patient physiological condition, and an electronic controller interconnected between the patient health monitor, the drug delivery controller, and the memory device storing the safety data set; wherein said electronic controller receives said signals and in response manages the application of the drugs in accord with the safety data set.

Figure 1:
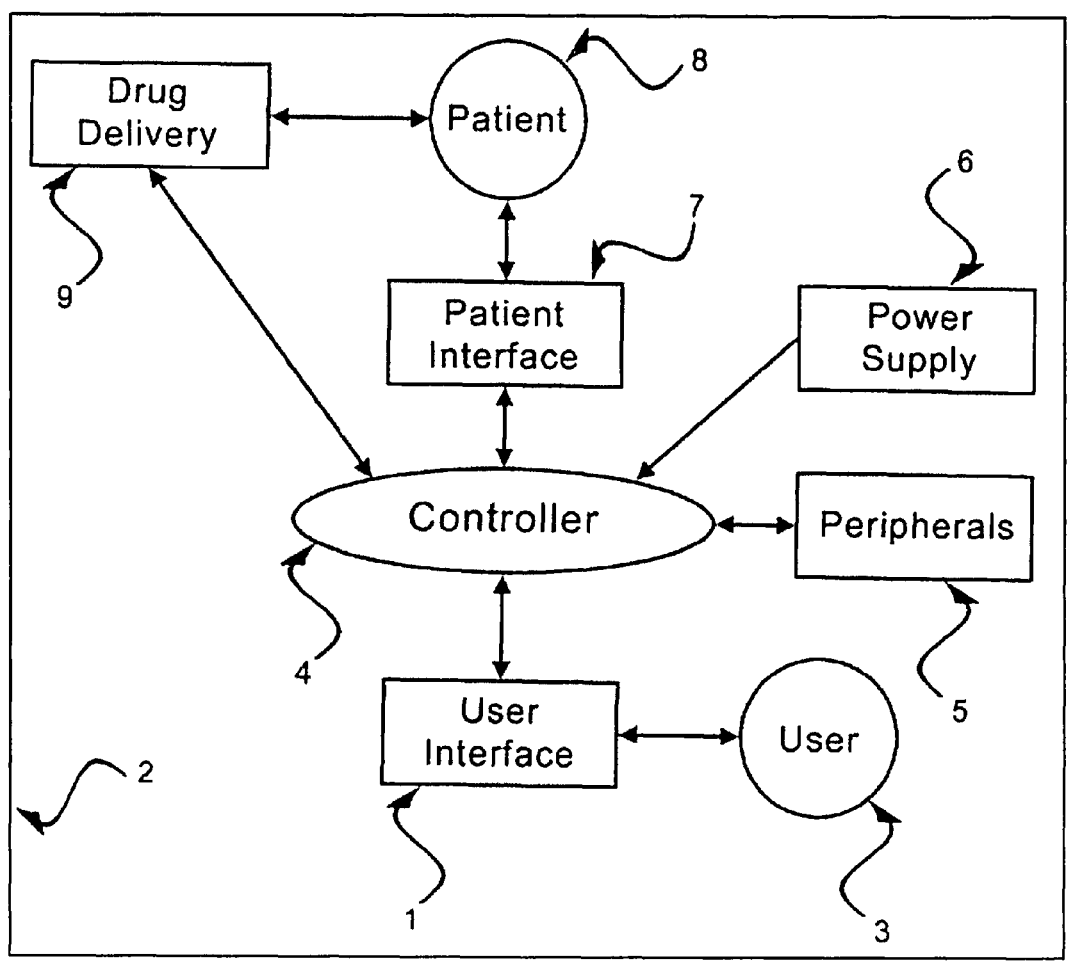
FIG. 1 illustrates a block diagram depicting an embodiment of a sedation and analgesia system for use with a user interface in accordance with the present invention

FIG. 1 illustrates a block diagram depicting one embodiment of such a sedation and analgesia system 2 in accordance with the present invention having UI 1, electronic controller 4, peripherals 5, power supply 6, patient interface 7, and drug delivery 9, where sedation and analgesia system 2 is operated by user 3 in order to provide sedation and/or analgesia to patient 8. Sedation and analgesia delivery system 2 for use with UI 1 of the present invention may be used with removable or disposable drug vials and reusable or disposable drug cassettes. Delivery system 2 may also be provided with automated responsiveness testing (ART), an example of patient interface 7, of patient 8. Examples of the ART function of delivery system 2 is described in U.S. patent application Ser. No. 60/342,773 filed Dec. 28, 2001 and incorporated herein by reference.

Various drugs, such as propofol, remifentanil, ketamine, dexmedetomidine, fentanyl, morphine, nitrous oxide, etc., may be administered by or used in conjunction with delivery system 1. Merely for illustrative purposes, UI 1 is herein described as it may be used with a system administering propofol. UI 1 provides the clinician user 3 control of the various features and capabilities characteristic of sedation and analgesia delivery system 2, including infusion algorithms that modify predicted effect-site concentrations of drugs. Examples of such features include the drug delivery modes and drug states described in U.S. patent application Ser. No. 10/208,183, filed Jul. 31, 2002 and incorporated herein by reference.

Many of the aspects of UI 1 are designed to be useful to a clinician who may or may not be experienced with sedation and analgesia to easily operate sedation and analgesia delivery system 2, while possibly being multi-tasked. One general feature of UI 1 that provides such utility is the consistent and continuous alerting of user 3 whenever the safety algorithms of delivery system 2 have been changed from their default settings. Another general feature of UI 1 is the requirement made of user 3 to confirm certain actions that he takes so as to give him the additional opportunity to check that only those actions that are truly intended are the ones implemented by delivery system 2. Common to this and all other confirmation screens of UI 1 is that the position of a confirmation touch button to be touched by user 3 to confirm his previous initiation command may not be displayed in the same area of the touch screen as the initiation button user 3 first touched to initiate the command. This difference in positioning may ensure that user 3 does not automatically or accidentally touch and approve the confirmation button merely because his finger was left in the same position on the screen as the initiation button. Also, if the positions of the initiation and confirmation touch buttons are at different locations, the positions of the initiation and confirmation touch buttons relative to each other may be consistent across different sets of initiation/confirmation touch buttons.

Another general feature of UI 1 is that certain information displayed to user 3 is grouped or is positioned for display to user 3 in a manner such that meaning may be drawn from the grouping or position or color scheme. Examples of these general features are expressed by the particular embodiments of UI 1 described below.

Figure 2:
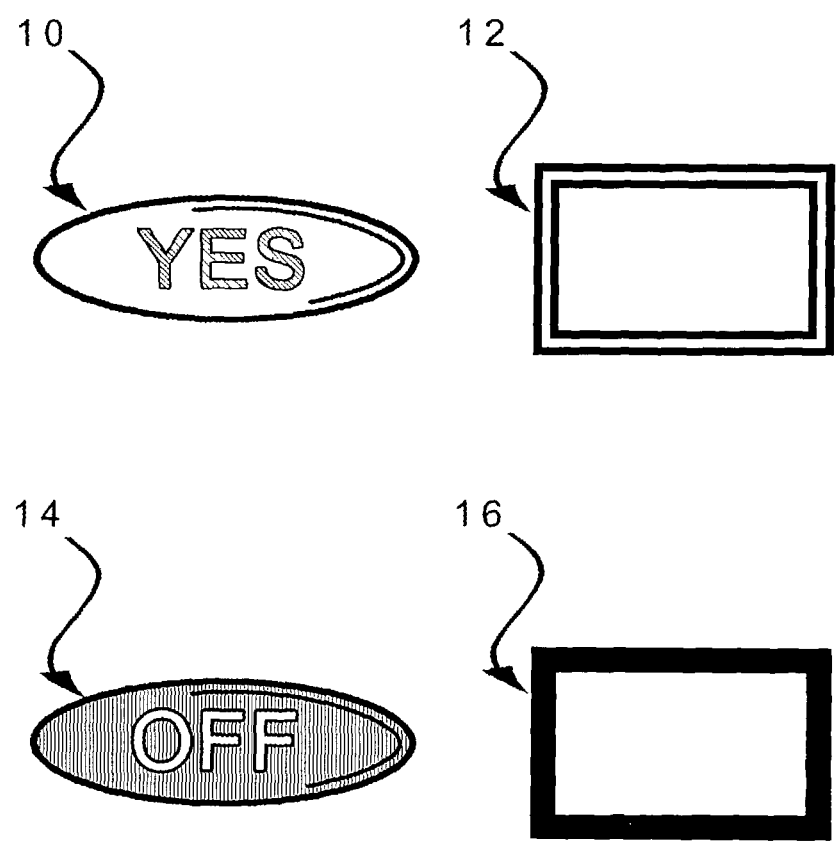
FIG. 2 shows examples of touch sensitive buttons and text entry touch boxes that may be used with the display of the present invention.

FIG. 2 shows areas of a touch screen input device 90 that may be provided for user 3 to interact with the software of delivery system 2 in a context sensitive, direct and intuitive manner which may not be possible by other types of input devices (fixed membrane keypads for example). These areas are touch sensitive and may be presented to user 3 as 3-D buttons 10 or as text entry touch boxes 12. The areas vary depending on the context and format of the information displayed at any given time to user 3. Entry of commands by user 3 may be accomplished by touching a 3-D box designated to such commands. Entry of data may be accomplished by touching a desired text entry box 12 and then entering the data via a membrane keypad or via a touch box keypad displayed on the screen.

FIG. 2 also shows that confirmation to user 3 of his text entry box activation may be made by delivery system 2 by displaying audio and/or visual feedback via UI 1. For instance, when touched, the appearance of a 3-D touch button 12 may be altered with a reverse image 14 or other modification. Visual feedback for text entry box activation may be provided by a highlighted text entry box 16 and/or by the appearance of a cursor. A sound such as an audible click may also play upon a text entry box's activation to further reinforce user feedback. When user 3 lifts his finger from a button, the system activates the function and provides an audio cue. If user 3 slides his finger off the button, the system un-highlights the button with no further action taken.

Figure 3:
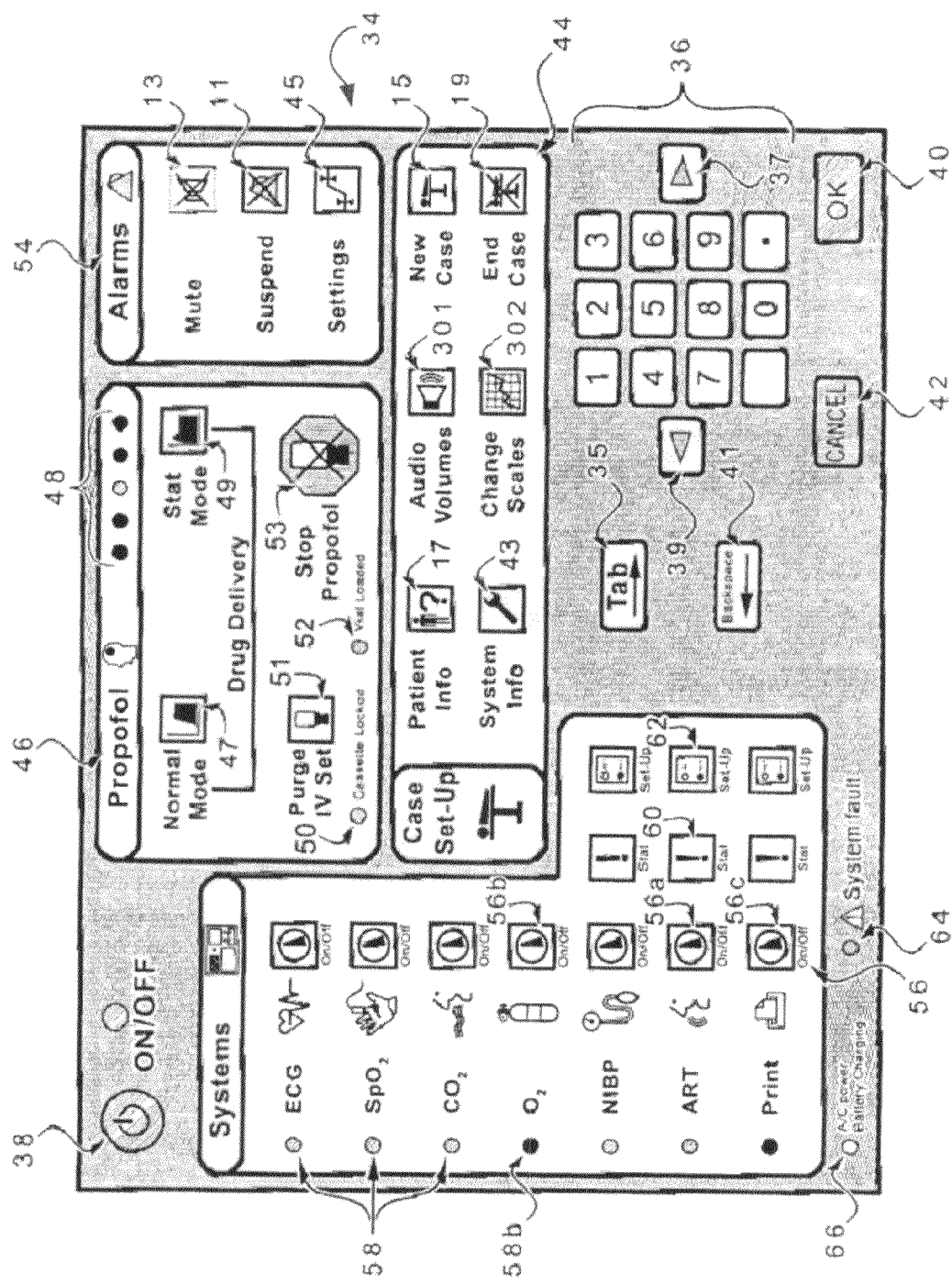
FIG. 3 shows an example of a keypad according to one embodiment of the present invention.

FIG. 3 shows a fixed membrane keypad 34 that may be provided on the console of delivery system 2 to allow user 3 to enter data and activate critical functions. The keys on membrane keypad 34 may have a ridge surrounding each of them to provide for their tactile location. Some special or often used membrane keys (for example, among others, "OK", "Cancel", "<", ">" and the number "5" at the center of a telephone style array of numbers) may have distinguishing tactile elements like raised dots, dashes or other such structures, to allow user 3 to know which membrane key is being touched without actually needing to look away from the touch screen display to look at the keypad. Membrane keys may also have activation feedback via a physical movement of the membrane followed by a tactile click. Delivery system 2 may also play an audio tone upon activation of a key of UI 1. These features allow user surety that a function has been activated upon his pressing of a button on keypad 34 Keypad 34 may receive overlays printed in various languages that can be easily swapped by user 3.

As shown in FIG. 3, keypad 34 may include standard numerical keypad 36, tab 35, forward arrow 37, backward arrow 39 and/or backspace 41 for data entry. A system On/Off or On/Standby button 38 is provided that when activated causes delivery system 2 to go into an activation sequence if previously inactive or into standby mode and shutdown sequence if previously active. Many necessary functions of delivery system 2 may have dedicated buttons on membrane keypad 34 for their direct activation. These buttons may be labeled by both text and icons and may also be associated with a colored LED that when lit indicates the corresponding function is active. Hard buttons for affirmative 40, and non-affirmative 42 replies may be included on the keypad to correspond to "OK", "No" and "Cancel" touch buttons on the touch screen. If the touch-sensitive functionality of touch screen 900 were to malfunction, these hard keypad buttons would serve to allow user 3 to still be able to respond to OK, No and Cancel requests on the various displays of UI 1, These buttons also provide ease of use in responding to system messages and screens.

Various systems keys may be provided on keypad 34 for the activation of system functions related to the initiation of a new sedation and analgesia procedure. Examples of such keys include patient Info 17, system info 43, change scales 302, audio volumes 301, new case 15, and end case 19. These keys are grouped within a common portion 44 of membrane keypad 34. The system functions associated with these keys are described in detail below. Various other keys may be provided for the activation of functions associated with the administration of propofol to a patient. Examples of such keys include purge IV line 51, normal mode 47, stat mode 49, and stop propofol 53. The system functions associated with these keys are described in detail below. These keys are grouped within common portion 46 of membrane keypad 34. A series of LEDs 48 may be provided adjacent to the Propofol delivery section of the keypad 46 which light in sequence, e.g., from left to right in the US and countries where text is read from left to right such that the amount of time that each LED is lit is inversely proportional to the rate of infusion of propofol currently being administered to patient 8. Alternatively, the array of LEDs may light up in a top to bottom sequence to reflect the mental model of a drip chamber usually associated with drug infusions. Another LED 50 may be provided adjacent to the propofol portion of the keypad that lights when a drug cassette is properly loaded into position on the housing of delivery system 2. LED 50 may light a particular color (e.g., green) when the cassette is positioned correctly and a different color (e.g., red) when the cassette is present but incorrectly loaded or is an invalid cassette as determined by system controller 4. A similar LED 52 may also be provided for representing the position and validity of a propofol vial.

Still referring to FIG. 3, various keys may be provided for the activation of system functions related to alarms. Examples of such keys include, among others, mute alarms 13, suspend alarms 11, and alarm settings 45. The system functions associated with these keys are described in detail below. These keys are grouped within a common portion 54 of membrane keypad 34.

Keys 56 may be provided for the activation of patient health monitors such as ECG, SpO$_2$, and CO$_2$ monitors. A switch such as an on/off toggle key 56 for each monitor allows the user to individually turn on or turn off each monitor. An associated indicator such as an LED 58 may be provided for each monitor that lights when the monitor is on.

An on/off toggle key 56a may also be provided for the ART function of delivery system 2. ART stat key 60 may be provided adjacent to the on/off button 56a that when activated causes delivery system 2 to turn the ART query device on and immediately administer a responsiveness test. At the user's request, the ART stat function facilitates patient learning of how to respond to a responsiveness test by allowing the user to initiate a test at any time even prior to the initiation of sedation and analgesia and even for mere instructional purposes or for setting a baseline ART response time. Set-up key 62 for the ART may be included on the keypad adjacent to toggle key 56a and stat key 60. ART set-up is described in detail below.

Similar on/off, Stat, and set-up keys may be provided for the non-invasive blood pressure (NIBP) function of the system. Stat NIBP and NIBP set-up are described in detail below. Similar on/off, stat, and set-up keys may also be provided for the print function of the system. When the stat print key is activated, a stat printout screen (FIG. 31) is displayed to the user. Print set-up is described in detail below. LED 64 that when lit represents an overall system fault and/or LED 66 that when lit represents that A/C power is present and the system battery is charging may also be provided with membrane keypad 34.

The individual on/off hard buttons for the ECG, SpO$_2$, CO$_2$, NIBP and ART monitors allow monitors to be individually turned off to adapt the system to the existing monitoring equipment like turning the NIBP monitor off if an invasive blood pressure monitor is already available in a cardiac catheterization lab. Being able to turn off individual monitors as they are removed from the patient at the end of the case also reduces the incidence of inappropriate and irritating alarms and allows capture and printing of baseline data before the procedure and subsequent suspension of the individual monitors while waiting for the procedure to start, without inappropriate alarms. This feature of UI 1 also allows user 3 to not use certain monitors in particular cases when patient physiological conditions indicate it is inappropriate. Another context of false and inappropriate alarms is when the monitors are on but a patient is not connected. For example, a CO$_2$ monitor may sound an apnea alarm if there is no exhaled CO$_2$ above a certain threshold for a given amount of time. UI 1 allows the user to turn off the monitors or suspend the alarms while a patient is not connected to the sedation and analgesia machine to reduce the incidence of false alarms.

FIG. 3 also shows on/off toggle key 56b which may also be provided for a supplemental O$_2$ delivery system. Associated LED 58b may be provided that lights when the supplemental O$_2$ delivery system is on. Automated printing may be selected or de-selected via a print on/off button 56c.

Figure 4:
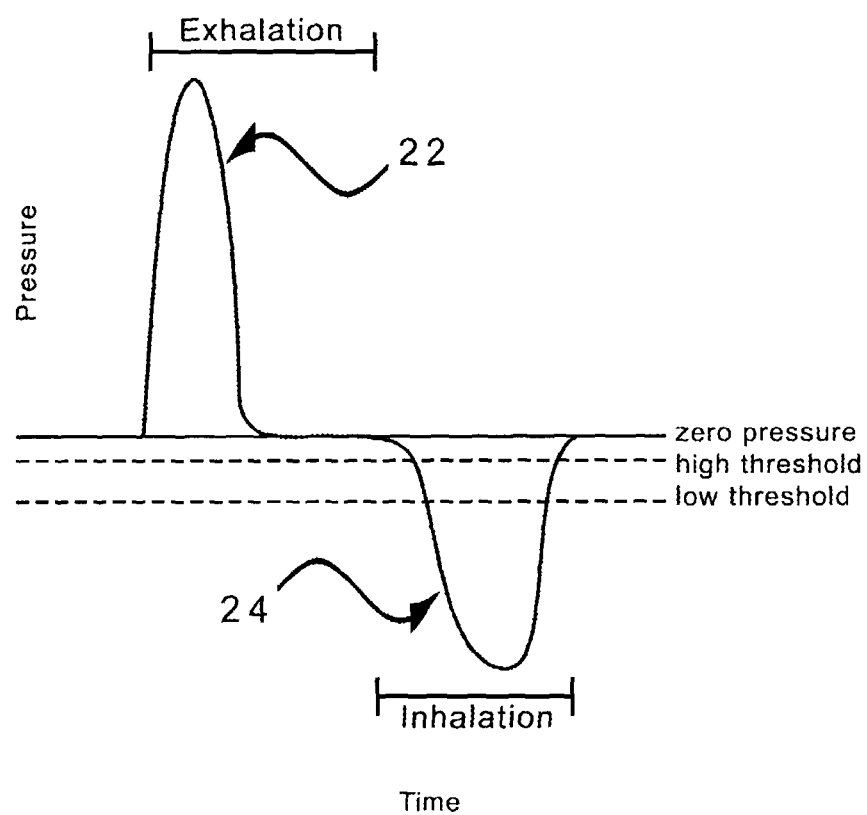
FIG. 4 shows an example patient respiration pressure curve according to one embodiment of the present invention

FIG. 4 shows a respiration pressure curve that depicts when the supplemental O$_2$ delivery system activates each of the high and low fixed flow rates of O$_2$. When the supplemental O$_2$ delivery system registers no sub-ambient or positive pressures, i.e., the patient is either apneic or is breathing through his mouth, for a certain period (e.g., at least 30 seconds), it causes a fixed medium flow rate of O$_2$ to flow to the patient. When both nasal and oral capnometers detect no respiratory rate for at least two minutes during a period of medium flow rate, the supplemental O$_2$ delivery system turns off the supplemental O$_2$ delivery to conserve O$_2$ This system provides the automated delivery of supplemental O$_2$ to aid patient oxygenation according to an O$_2$ administration algorithm. By this algorithm, the system begins to register pressure variations determined from a comparison of the values sampled at the patient's left and right nares (as read by nasal pressure transducers) upon the capnometer's first report of a respiration rate that is greater than zero. The system causes a fixed high rate of O$_2$ to flow to the patient when it generally determines there is a sub-ambient pressure 24, i.e., when the patient is inhaling, and it causes a fixed low rate of O$_2$ to flow to the patient when it determines there is generally a positive (supra-ambient) pressure 22, i.e., when the patient is exhaling so that CO$_2$ can be simultaneously measured with supplemental O$_2$ delivery and displayed in the form of a real time capnogram plus derived information such as respiratory rate and end-tidal CO$_2$.

By default, the supplemental O$_2$ administration system is off at the beginning of a new patient procedure. User 3 must take the initiative to turn on the O$_2$ flow prior to the initiation of a new sedation and analgesia procedure before the O$_2$ administration algorithm will begin the automated delivery of supplemental O$_2$. At the beginning of a new procedure, user 3 is presented a display screen prompting him to make the explicit decision of whether or not to turn on the O$_2$ flow. The user is thus in position to avoid any oxygen supplementation if he has reason to be concerned about a patient with hypoxic drive to breathe syndrome, to whom any supplemental oxygen delivery could be harmful. By ensuring that the user must first make such an explicit decision before any supplemental O$_2$ is administered to a patient, the supplemental O$_2$ administration system minimizes both the risk that the user will inadvertently start drug administration at a time when oxygen supplementation has not begun and the risk that a user will inadvertently start oxygen supplementation to a patient with hypoxic drive to breathe syndrome.

Figure 5:
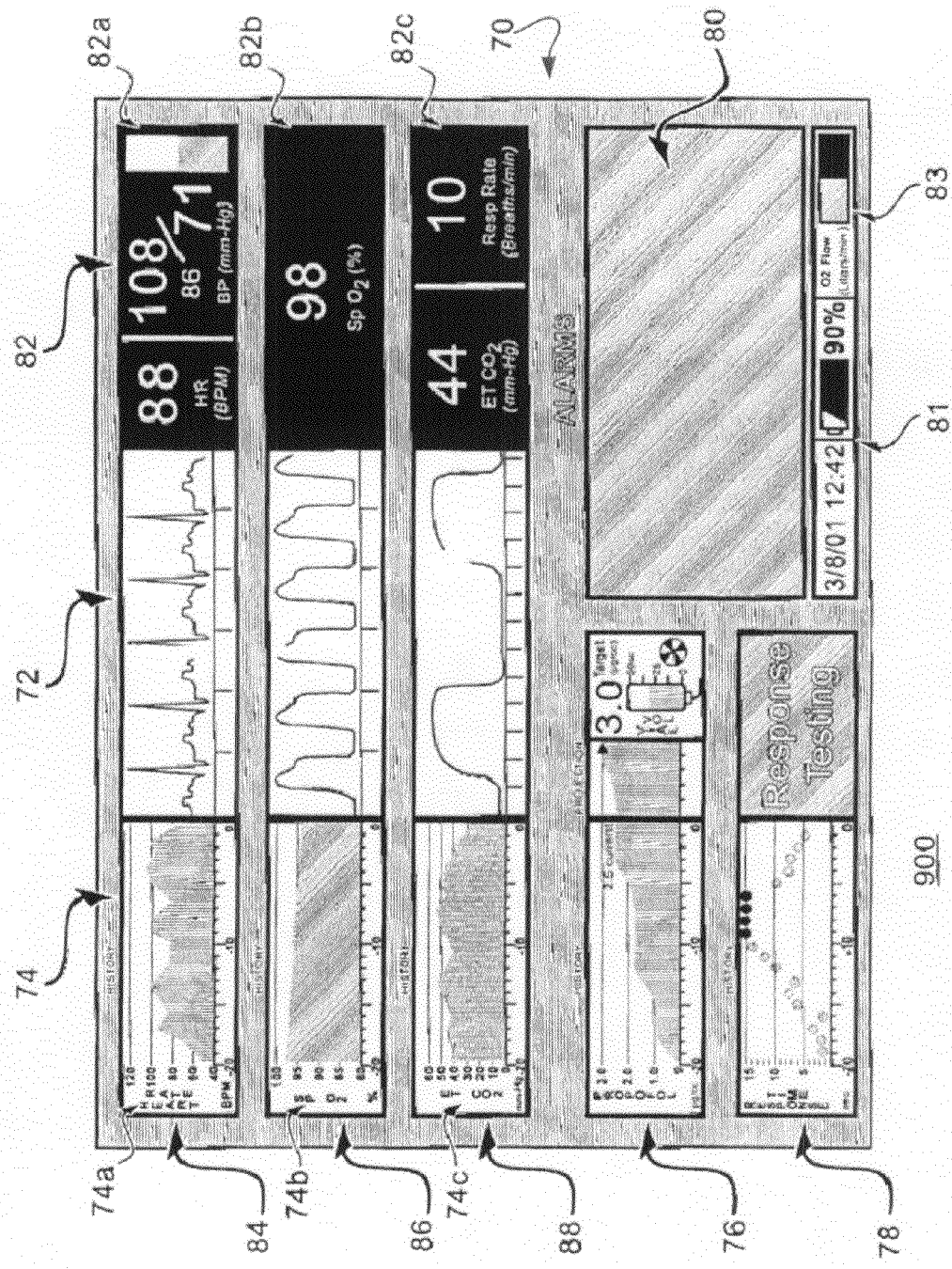
FIG. 5 shows an example monitoring display of the user interface according to one embodiment of the present invention.

FIG. 5 shows an example of touch screen 900. Touch screen 900, in combination with a comprehensive collection of hard keys of keypad 34 (FIG. 3), implemented via structures such as a membrane keypad, is designed to provide, to the extent possible, a flat command structure so that optimally a user should not have to search more than one layer or sub-menu deep for any particular action that he might wish to initiate. Critical actions, such as stopping the flow of drugs, are implemented via hard keys such as stop propofol button 53 (FIG. 3), so that they are always instantly visible and available. Furthermore, by implementing critical actions as hard keys, initiation of a critical action is not dependent on proper functioning of a touch screen or soft button. This unique hybrid touch screen/hard key combination provides the advantages of both input modalities while also providing redundant means for data entry, for increased patient safety, in the event of malfunction of the touch screen as a data entry device.

FIG. 5 shows primary monitoring display 70 on touch screen 900. Primary monitoring display 70 may provide any or all of (1) display 72 of signals representing the critical parameters of the patient; (2) display 74 of historical data of each of the critical parameters of the patient; (3) display 76 of propofol infusion information and effect-site levels; (4) display 78 of ART information; (5) display 80 of any system advisories and/or any patient state alarms; (6) display 81 of the date and time and the delivery system's power status; and (7) iconic display 83 of the status of supplemental oxygen administration (See FIG. 4) that communicates the different levels of $O_2$ flow being delivered during different states of patient respiration (inhalation, exhalation, apnea, pure mouth breathing). Primary monitoring display 70 is available to be shown to user 3 at all times after system start-up. Other displays may be presented as pop-up windows on touch screen 900 overlaying the primary monitoring display 70.

Primary monitoring display 70 may include digital display 82 of the current value for each of the critical parameters of the patient that is displayed in corresponding parameter data boxes. These boxes are positioned on primary monitoring display 70 such that the information displayed therein may always be available to be shown to user 3 even when various pop-up overlaying windows are displayed. The background color of the parameter data boxes and the color and size of the characters representing the parameters are chosen so as to be easily read by user 3 from a distance allowing monitoring by users who are physically distant from UI 1. For example, the background may be black while the characters are white. The parameter boxes may be grouped within one portion of primary monitoring display 70 so that user 3 may reference all of the parameters easily and without having to look to more than one location for all of the critical data. The parameter values may be grouped according to related physiological functions.

Still referring to FIG. 5, Primary monitoring display 70 has information organized in meaningful sets of data that represent physiological systems (e.g., hemodynamic/cardiovascular 84, oxygenation 86 and respiratory ventilation 88) whereas once the geography or semantic of the information has meaning, the alarming parameters are color-coded in context when they are out of nominal ranges stored in a safety data set. For example, if the BP and HR (which are both hemodynamic/cardiovascular parameters) are non-nominal or alarming, then in context, the background color will be coded as to how abnormal they are, e.g., red if severe and yellow if cautionary. This color-coding allows user 3 to assess alarming parameters in the context of meaningfully grouped data relevant to physiological systems (hemodynamic/cardiovascular 84, oxygenation 86, respiration/ventilation 88, drug levels 76 and patient responsiveness 78). Many clinicians work in different office surgery, ambulatory and outpatient settings and may become confused by inconsistent user interfaces. UI 1 is consistent such that different machines of the same design at different locations exhibit the same look and feel to the itinerant user.

It is contemplated that any critical parameter of the patient sensed by an appropriate device and relevant to the administration of propofol or other sedative or analgesic agents or the delivery of sedation and analgesia may be used by delivery system 2 and displayed to user 3 via UI 1. The following parameters may be displayed to the user: heart rate, blood pressure (systolic, mean, diastolic), $SpO_2$, end tidal $CO_2$, and respiratory rate. In an example of how these parameters may be grouped in primary monitoring display 70, the heart rate and blood pressure readings may be displayed in cardiovascular parameter box 82a (shown in more detail in FIG. 6), $SpO_2$ is displayed in an oxygen parameter box 82b (shown in more detail in FIG. 7), and end tidal $CO_2$ and respiratory rate are displayed in a $CO_2$ parameter box 82c (shown in more detail in FIG. 7).

Also shown in FIG. 5, current signals from patient monitors are displayed in real-time data boxes 72. These boxes may include ECG data 72a, $SpO_2$ monitor data 72b, $CO_2$ monitor data 72c. The signals may be displayed as color waveforms on a neutral background and may be updated at a regular rate (e.g., 3 Hz). Each signal may have a different waveform color (e g., red for ECG data 72a, green for $SpO_2$ monitor data 72b, and gray for $CO_2$ monitor data 72c). The color scheme adopted may vary according to the country where the device is used. For example, the above color scheme is adapted to the coloring convention for gases in the United States. The current zero time is indicated by a gap (i.e., erase bar) 72d in each waveform. This erase bar scrolls across each real-time data box 72 as the signals are updated. Time marks are displayed in a horizontal line at the top or bottom of any or all of the real-time data boxes 72. Time scale values exist as particular defaults in UI 1 for each signal and can be changed by the user.

Each real-time data box 72 may be displayed adjacent to the parameter data box 82 displaying the associated parameter values obtained from the corresponding monitor. For example, the ECG real-time signal 72a is shown adjacent to the cardiovascular parameter box 82a, the $SpO_2$ real-time signal 72b is displayed adjacent to the oxygen saturation parameter box 82b, and the $CO_2$ real-time signal 72c is displayed adjacent to the respiration parameter box 82c. The vertical scale for the $CO_2$ signal may be aligned with the scale of an adjacent $CO_2$ history graph 74c (described below). If a patient monitor is turned off, a message to that effect is displayed in the corresponding real-time data box 72 in place of the signal waveform. Whenever a gas calibration is taking place, a message to that effect (e.g., the letters "CALIBRATION") will be displayed by the system in or near the $CO_2$ real-time signal box 72c such that the user may easily notice that a calibration is taking place at the same time that he looks to reference the $CO_2$ real-time signal.

If the NIBP cuff is placed on the same arm as the pulse oximeter probe, an "NIBP CYCLING" message is placed over the $SpO_2$ real-time data box 72b while the NIBP cuff is cycling and the $SpO_2$ alarm will be disabled while the NIBP cuff is inflating. UI 1 also provides a means for the user to inform the system that the NIBP cuff is on the same arm as the pulse oximeter probe such that the disabling of the $SpO_2$ alarm during NIBP cycling only occurs if the pulse oximeter probe and NIBP cuff are on the same arm.

The tone or frequency of the beep emitted with each pulse by the pulse oximeter corresponds to the $SpO_2$ value. The lower the $SpO_2$, the lower the frequency of the beep. If the $SpO_2$ monitor is turned off or not working but HR is available from the ECG monitor, there will be no beep with each heart beat because a default or neutral tone might be inappropriately associated with an $SpO_2$ value or a functional $SpO_2$ monitor when none is actually available.

FIG. 5 also shows that primary monitoring display 70 may include history graphs 74 exhibiting the recent trend of each of certain of the critical parameters. A heart rate history graph 74a, a pulse oximetry history box 74b, and an $ETCO_2$ history box 74c may be displayed. Historical values for these parameters may be displayed as colored solid graphs with a horizontal scale of time set at a default within the system that is changeable by the user. The color may be chosen to match the color used for the waveforms of the real-time data boxes 72. Vertical scales relevant to the particular parameters will also be set to defaults within the system that are changeable by the user. The vertical scale of some of the history graphs 74, like $CO_2$, may be the same as the scale of the corresponding real time data boxes 72. Horizontal and/or vertical scale lines may be displayed on each history graph 74.

The history graphs 74 may be positioned adjacent to the corresponding real-time data boxes 72, which are positioned adjacent to the corresponding parameter data boxes 82 on the primary monitoring display 70, thereby creating physiological data lines 84, 86 and 88. Each physiological data line contains related information positioned in a single easily referenced area of the primary monitoring display 70 that can be quickly scanned and referenced by the user.

The physiological data lines 84, 86 and 88 may be positioned on the primary monitoring display 70 in such a manner as to aid user 3 in interpreting the meaning of the data they display. For example, the cardiovascular line 84 may be placed adjacent to pulse oximetry line 86 so that the user can with one quick glance assess whether there is a correspondence between the current data graphed in the two lines. A consistent timeline is used for corresponding physiological data lines. This correspondence or lack thereof may be useful to the user in determining whether an alarm state existing with the data in one line is a real and serious alarm or whether it is an artifact. If an alarm exists based on the pulse oximetry data and there is a one-to-one correspondence in the oximetry and ECG plots 72a and 72b, then the alarm is likely real, but if there is not a one-to-one correspondence then the alarm is likely an artifact.

FIG. 5 shows an example of the physiological data lines 84, 86 and 88 being positioned adjacent to one another and in a useful manner. FIG. 5 also shows an example of a therapy control (propofol) being placed next to the monitored parameter (ART) that it affects in that propofol display 76 is set next to ART display 78.

Figure 6:
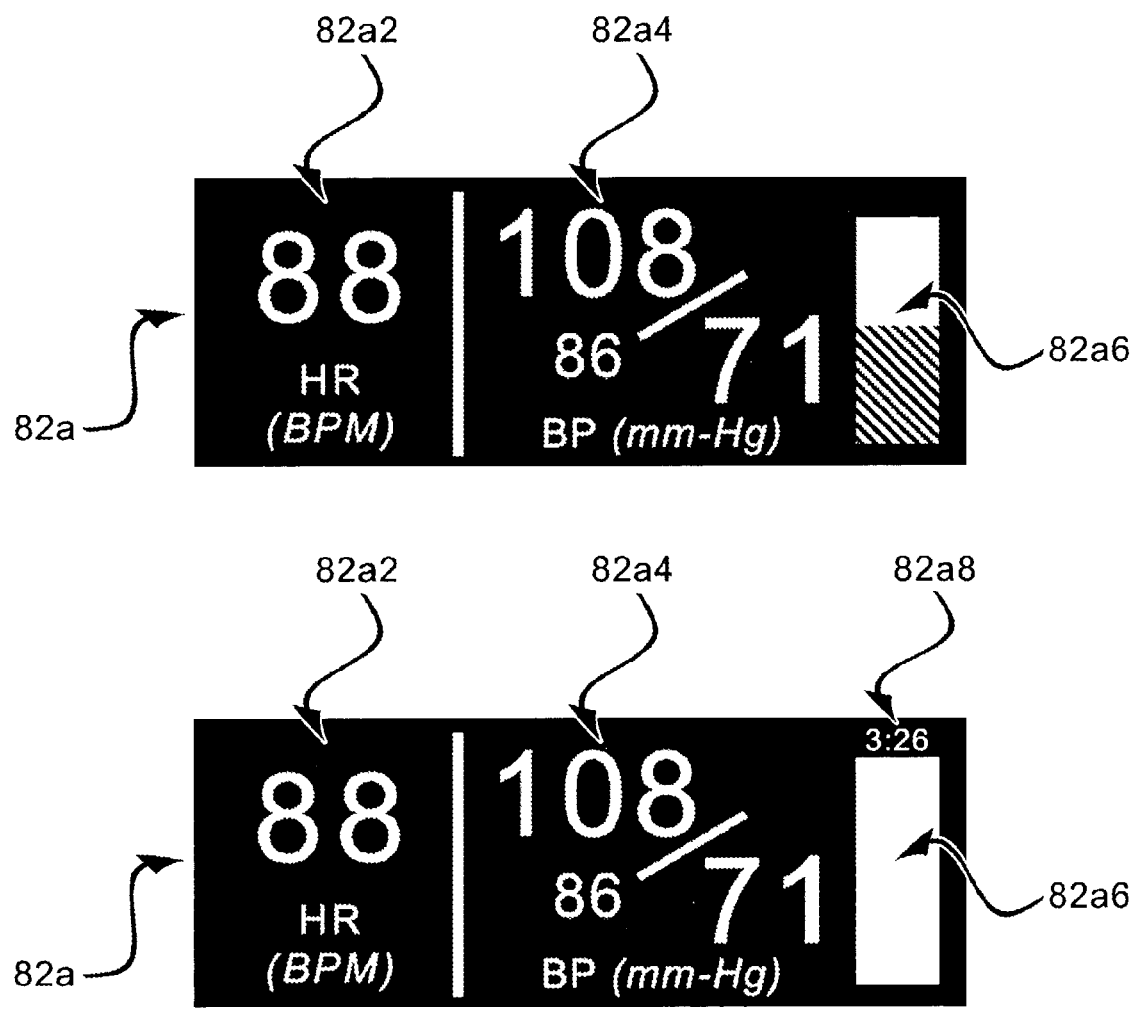
FIG. 6 shows example displays of cardiovascular parameter boxes according to one embodiment of the present invention.

FIG. 6 shows heart rate displayed in heart rate box 82a2 within cardiovascular parameter box 82a. Heart rate may be primarily obtained from an ECG monitor but may also be obtained from the $SpO_2$ monitor when the ECG monitor is off, when no valid data is being received from it, or when the user specifies the $SpO_2$ monitor as the preferred heart rate source. If there is no ECG data and no available pulse rate data from the $SpO_2$ monitor, then UI 1 will display an appropriate indication (e.g., "—") in place of the heart rate parameter in heart rate box 82a2. Also in cardiovascular parameter box 82a, the last systolic blood pressure reading taken from the patient is displayed in blood pressure box 82a4. Other parameters that may also be displayed in the blood pressure box include: the latest mean blood pressure, analog thermometer bar 82a6 displaying the NIBP cuff pressure, and the time elapsed 82a8 since the last cuff inflation.

FIG. 6 shows that in embodiments on UI 1 in which thermometer bar 82a6 is displayed, when the cuff is taking a blood pressure reading, the bar rises as cuff pressure increases and falls as pressure is released. When no blood pressure reading is available (i.e., when the NIBP monitor is off), the system will display an appropriate indication (e.g., "—") in place of the blood pressure parameter in blood pressure box 82a4.

Figure 7:
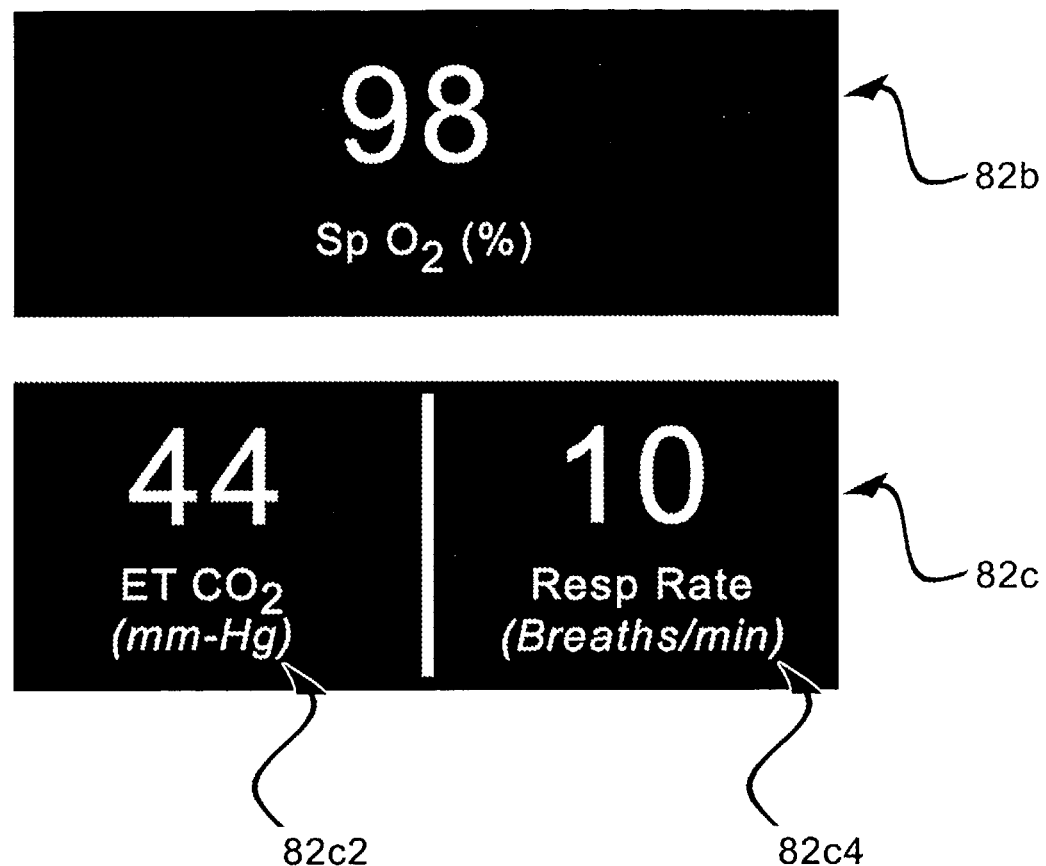
FIG. 7 shows example displays of an oxygen parameter box and a $CO_2$ parameter box according to one embodiment of the present invention.

FIG. 7 shows more detail of oxygen parameter box 82b. If the $SpO_2$ monitor is off, absent or malfunctioning or if there is no valid data being received from it, the system will display an appropriate indication (e.g., "—") in place of the $SpO_2$ parameter in oxygen parameter box 82b.

FIG. 7 also shows the end tidal $CO_2$ ($ETCO_2$) parameter displayed in $ETCO_2$ box 82c2 within the $CO_2$ parameter box 82c. The $ETCO_2$ parameter displayed may be the highest value obtained from a capnometer from either patient sample site, oral or nasal, during a particular period of time (e.g., the last 25 seconds). The respiratory rate displayed in respiratory rate box 82c4 within the $CO_2$ parameter box may be a value averaged across the last number (e.g., four) of breaths as obtained from the capnometer. If the capnometer is off or if there is no valid data being received from it, the system will display an appropriate indication (e.g., "—") in $ETCO_2$ box 82c2 and respiratory rate box 82c4.

For data selection, the $CO_2$ waveform values gathered from each patient sample site, oral or nasal, of the capnometer may be summed over a particular period of time (e.g., 15 seconds). Upon such summation, the $CO_2$ parameter displayed in $ETCO_2$ box 82c2 is the value taken from the one capnometer sample site having the greater sum over the particular period of time. This comparison is biased in favor of the nasal sample. In an example of such biasing, data from the oral sample site is displayed only if it exceeds the nasal data by at least a factor of 1.5 while data from the nasal sample site is displayed merely if it exceeds the oral data. The nasal capnometer may switch between sampling from one nare to the other, based on the strength of the pressure signals seen in each of the nares. If the average pressure value (e.g., the average of the last four values taken) of one nasal pressure sensor exceeds some minimum value and exceeds the average pressure value of the other sensor by at least a factor of 3, delivery system 2 will switch to that first nasal sensor for the $CO_2$ waveform display as long as the system is currently displaying nasal capnometer data. The respiratory rate displayed (and used for generating alarms) is based on the same input from the capnometer, oral or nasal, whose waveform is being displayed. The $ETCO_2$ value displayed (and used for generating alarms) will be the larger of the two.

Whenever a gas calibration is taking place, a message to that effect (e.g., the letters "CALIBRATION") will be displayed by the system in or near the $ETCO_2$ and/or respiration rate boxes such that the user may easily notice that a calibration is taking place at the same time that he looks to reference the parameter for either of $ETCO_2$ or respiratory rate. The message is thereby positioned where the user would naturally look for current data from the capnometer and provides an instant and unmistakable indication that the absence of data from the capnometer during a period of calibration is due to the calibration process rather than due to a severe physiological anomaly.

Figure 8:
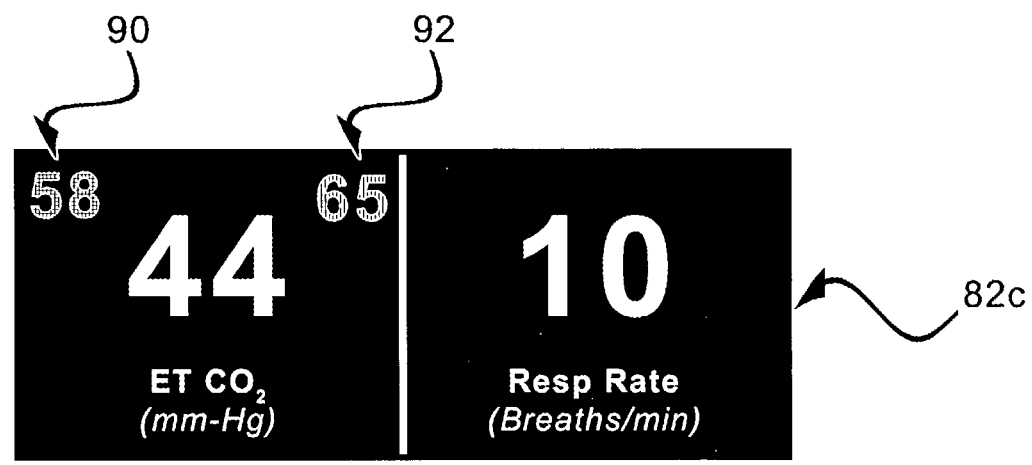
FIG. 8 shows an example display of a parameter data box displaying user-changed non-default alarm settings according to one embodiment of the present invention.

FIG. 8 shows an example of a parameter data box 82c displaying user-changed non-default alarm settings. Whenever a default alarm setting has been changed by the user (described below), the new alarm settings for that parameter will be displayed adjacent to the parameter within that parameter's data box such that the user can determine at a glance if the basic alarm functionalities of the system have been altered from their default settings. This feature is particularly important when there are multiple concurrent users of a complex medical system. The alarm limit values may also be displayed whenever the user selects to show the alarm limits from the alarm settings display (described below). The new non-default value for a caution alarm 90 may be displayed in the caution alarm color (e.g., yellow) and the new non-default value for the warning alarm 92 may be displayed in the warning alarm color (e.g., red) when the parameter is not in an alarm state.

Figure 9:
FIG. 9 shows an example display of a parameter box with caution and warning alarms active for two, parameters according to one embodiment of the present invention.

As shown in FIG. 9, when the parameter is in an alarm state and the background color of the parameter data box changes to the alarm color (described below), the colors of the non-default values change to a color that can be easily read against the new background. The new values may be offset from and smaller than the text of the current value of the parameter displayed in the data box.

Figure 10:
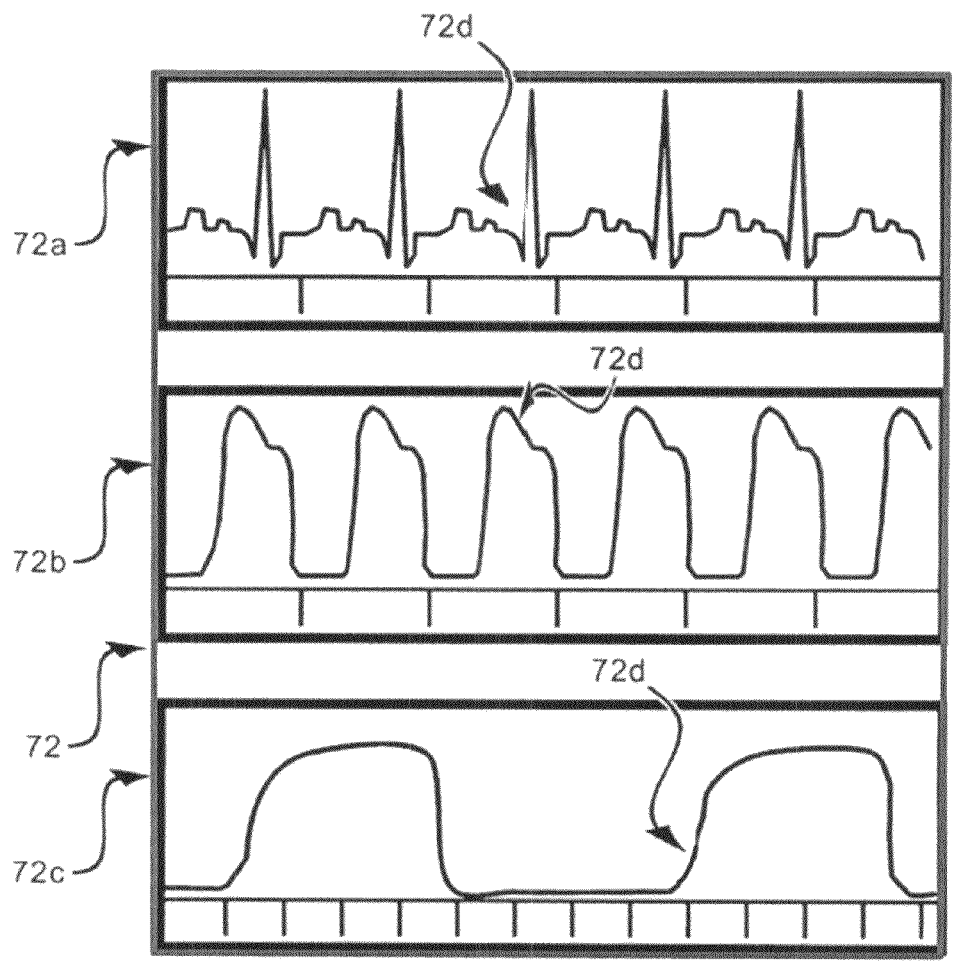
FIG. 10 shows example displays of real-time data boxes according to one embodiment of the present invention.
Figure 11:
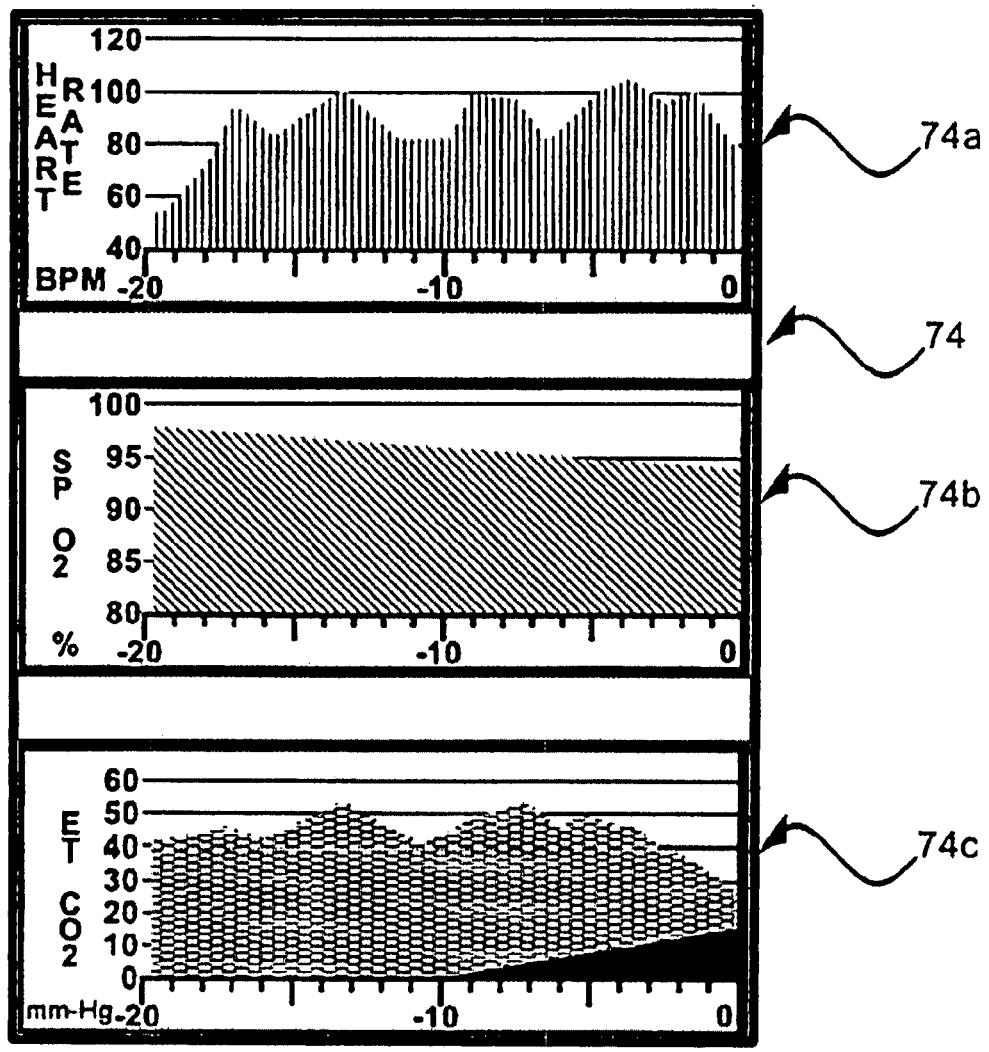
FIG. 11 shows example displays of parameter history boxes according to one embodiment of the present invention.

FIG. 10 shows examples of real-time data boxes 72 in more detail. ECG real-time signal 72a, SpO$_2$ monitor data 72b, and CO$_2$ monitor data 72c are shown. Erase bar 72d is also shown FIG. 11 shows examples of heart rate history graph 74a, pulse oximetry history box 74b, and ETCO$_2$ history box 74c.

Figure 12:
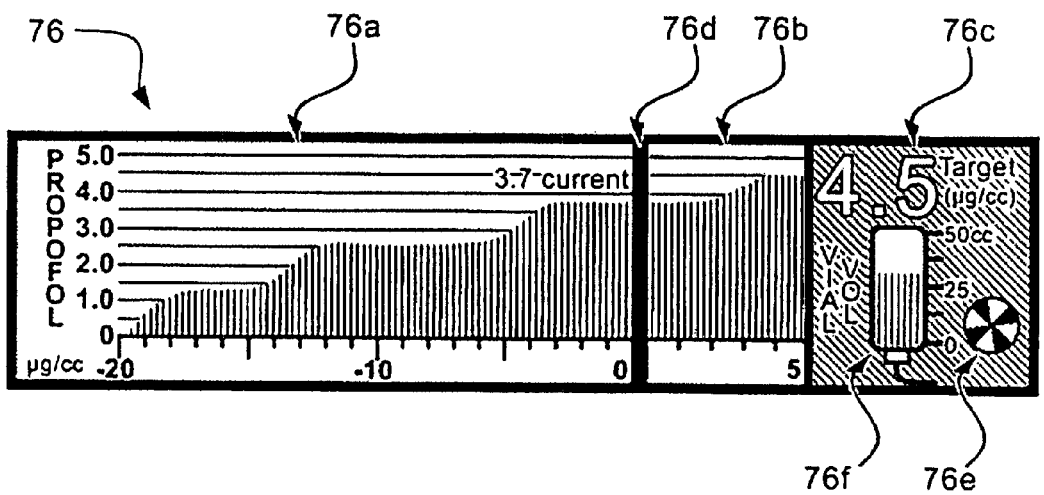
FIG. 12 shows an example display of a propofol infusion box according to one embodiment of the present invention.

FIG. 12 shows propofol infusion box 76 in detail. Propofol infusion box 76 may show information about the projected, current, and historical calculated effect-site concentrations of propofol. The historical calculated effect-site levels of propofol for a particular period may be shown as a colored graph 76a to one side of a current line 76d and a colored projected target effect-site graph 76b may be shown to the other side of the line. The color of each graph may be the same, but the intensity of the color of the historical graph is different, e.g., less than the color of the projected graph 76b, to emphasize the difference between historical data and projected data. The horizontal scale of time is shown at either the top or the bottom of both graphs 76a and 76b where the times to the historical side of the current line 76d are shown as negative numbers. The scale of how much historical and projected data of effect-site level is displayed exists in default within the system but may be changed by the user. The vertical scale of calculated concentration of propofol at the effect-site also exists in default but is changeable by the user. The vertical scale may also increase when the user enters a new target effect-site level of propofol—insuring that the new level can be displayed on the graph. Scale lines may be displayed horizontally and/or vertically across both the historical and projected graphs. The current value of the calculated effect-site level of propofol may also be displayed next to the current line, i.e., overlaid on either the historical 76a or projected 76b graphs.

Adjacent to the graphs within propofol infusion box 76 is propofol settings box 76c. In this box, the system displays: the target effect-site level of propofol (while the system is in normal, or stat mode); the word "Target" or any other message relaying the fact to the user that the value of the effect-site level within the propofol settings box 76c is merely a target level; a rotating flow icon 76e which graphically indicates the current flow rate of propofol infusion, and an icon and/or graph 76f depicting the volume of propofol within the infusion vial. In one embodiment of the present invention, the volume icon 76f resembles an infusion vial and depicts a colored representation of the current level of propofol remaining within the vial. Graduated markings are shown next to the vial icon in order to determine the numerical value of the initial volume and the current volume. FIG. 12 shows an example display of propofol infusion box 76 when the propofol infusion is active.

Figure 13:
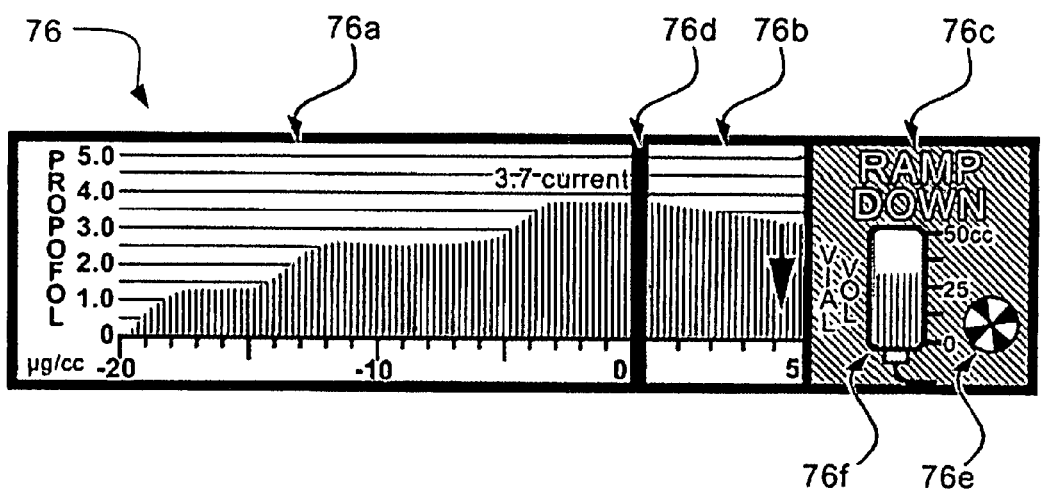
FIG. 13 shows another example display of a propofol infusion box according to one embodiment of the present invention.

FIG. 13 shows an example display of propofol infusion box 76. UI 1 clearly displays key drug administration states via propofol infusion box 76 to user 3. The states of drug administration may include such states as normal, ramp-down, and off. For example, in the ramp down mode, an appropriate message is displayed in place of the target effect-site level in the propofol settings box 76c and a downward arrow may be displayed over the projection graph 76b. FIG. 13 shows an example display of propofol infusion box 76 when the system is in ramp down mode. When the delivery system 2 is off and propofol is not being administered, the message "Off" or the like will be displayed in propofol settings box 76c and a different background color in the box than exists when propofol infusion is active will be shown. Historical graph 76a of drug administration and current line 76d are also shown.

Figure 14:
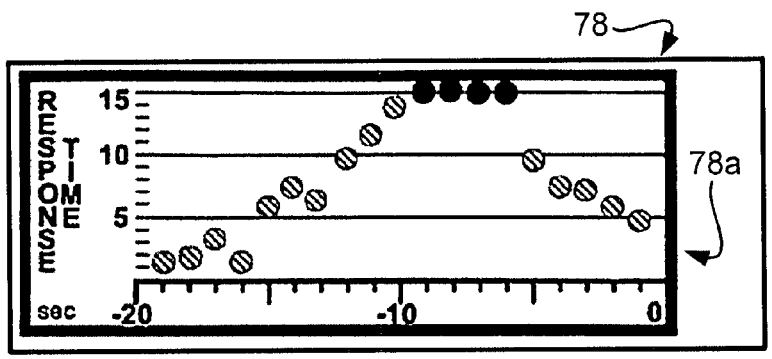
FIG. 14 shows an example display of an ART history section of a monitoring display according to one embodiment of the present invention.

FIG. 14 shows an example display ART information box 78 containing ART history 78a section. ART information box 78 may also contain ART status section 78b. Within the ART history section 78a, UI 1 may display a symbol for the patient's response to each ART query cycle plotted as the time interval between initiation of ART stimulus and the patient's response to the ART query cycle along the y-axis of a graph versus the time at which each ART test cycle was initiated along the x-axis. In the automated ART mode, patient responses occurring within a designated period of time t (e.g., 14 seconds) from the initiation of the query cycle are displayed as a symbol in one color, e.g. green, on the graph. A patient response that occurs more than t seconds (e.g., 14.5 or 20 seconds) from the initiation of the query cycle or that constitutes a failure to respond to the query cycle altogether will be displayed as a symbol in another color, e.g. blue. Any response time greater than t seconds or any failed response may be displayed on the y-axis at time t+1 (e.g., 15 seconds) seconds. Therefore, the vertical scale of the graph need only be t+1 seconds. FIG. 14 shows an example display of an ART history section 78a where five ART results exceeded t seconds (i.e., 14 seconds) from the initiation of the patient query cycle and thus are displayed at t+1 seconds (i.e., 15 seconds) along the y-axis. Affirmative responses to a prompted manual ART test will always be recorded and displayed at a particular time $t_{manual}$ (e.g., 5 seconds). As time progresses, the symbols representing recent ART results will scroll to one side of the ART history section 78a and will be dropped from the display after they are older than a given elapsed time. The scope of the x-axis scale determines when past ART results will be dropped from the display. The scale exists as a default in the system but may be changed by the user.

Figure 15:
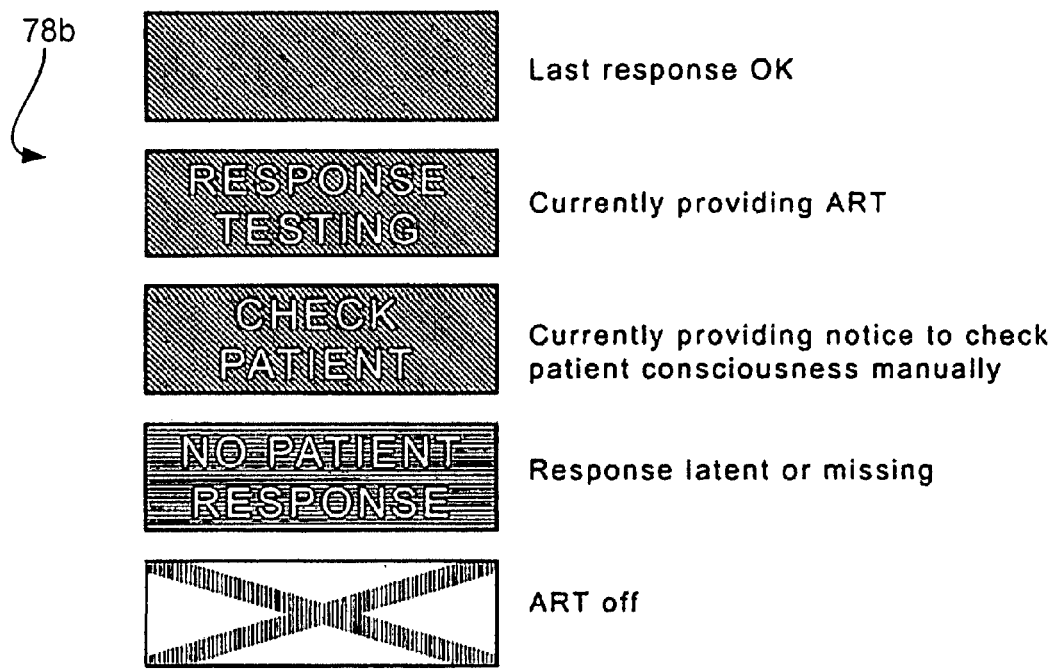
FIG. 15 shows example displays of an ART status section of a monitoring display according to one embodiment of the present invention.

FIG. 15 shows examples of ART status section 78b. ART status section 78b may show the words "Response testing" or "Responsiveness testing" on a particular color (e.g., green) background during the duration of the ART test cycle or period. The ART status section 78b shows a solid fill of a particular color (e g., green) following a patient response time within the designated time t seconds from the most recent ART query cycle. ART status section 78b shows a background of a different color (e.g., blue) and a relevant message, e.g., "No patient response", when the patient does not respond within t seconds from initiation of a query cycle or when the patient fails to respond to a query cycle altogether. ART status section 78b may also display a message when a query cycle is currently being administered. If the ART mode has been designated for a prompted manual check of the patient, a message will be displayed at each designated ART interval which alerts the user to assess the patient's condition. An audible tone may also be played by the system to prompt the user to manually check the patient. If the user does not provide information to the system regarding the patient's condition within a designated time limit, e.g., 45 seconds, the system will assume a non-responsive patient and may display a message indicating that there was no patient response received. User 3 may select to be prompted for manual responsiveness tests at the ART set-up preferences display (described below). This capability may be used when the user identifies the patient as lacking competency or cooperativeness. When the ART has been disabled, an appropriate symbol (e.g., a red "X") is displayed within the status section 78b.

When the user has activated automated responsiveness testing (either at the beginning of drug administration or upon the pressing of the ART on/off button 56a (shown in FIG. 3)), ART query cycles are presented to the patient per a certain interval. The interval between ART query cycles exists as a default period of time (e.g., three minutes) but may be changed by the user via the ART set-up preferences display (shown in FIG. 34), which is accessible by pressing ART set-up button 62 on membrane keypad 34. The system may also automatically present ART query cycles at a more frequent interval (e.g., every 15 seconds) than the default interval under certain conditions, such as when the user changes the current effect-site concentration. Responsiveness tests may also be automatically administered [outside of any interval] any time there is a warning or caution alarm for certain patient state parameters (e.g., low $SpO_2$, low heart rate, low blood pressure, or low respiration rate alarms). User 3 may also manually trigger an automated responsiveness test at any time by pressing ART stat button 60. When the user calls for a stat response test, the system resets the timer associated with the interval between ART query cycles and/or turns on the ART system if it had not been on when the user pressed stat ART button 60.

At any time the patient fails to respond to n, e.g., 2 consecutive automated responsiveness test cycles within the designated period, t seconds, the system may automatically go into a slow ramp down of propofol at a certain negative rate. The target dosage level indicated in the propofol infusion box 76 is then replaced with an indication of the ramp down state.

Figure 16:
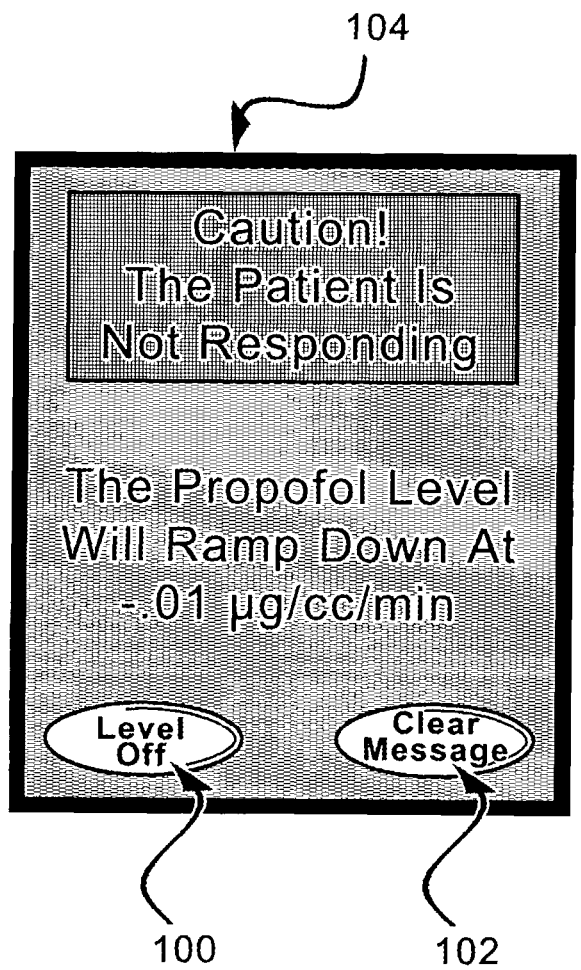
FIG. 16 shows an example display of a ramp down confirmation message according to one embodiment of the present invention.

FIG. 16 shows a ramp down confirmation message that may also be presented to user 3 for a short period of time during which the user may select a "level off" option 100 to cause the ramp down of drugs to cease and the target effect site level to be set at the current effect site level. Alternatively, the user may select a clear message option 102 to remove ramp down confirmation message 104 and allow the ramp down state to continue. If a short period of time elapses before the user selects either option, the system automatically clears the message. Also upon a patient failing to respond to a query cycle within the designated period, the system may play an auditory message to the user upon the initial failure of the patient to respond. This auditory message may be in the form of a verbal message such as "Loss of Patient Response" or may be another sound suggestive to the user that the patient has failed to respond to a query cycle. Should the patient timely respond to a subsequent query cycle but then fail to respond at some later time, the auditory message may again be played. ART status section 78b (FIG. 15) may show a message indicative of a failed response any time the patient does not respond to a query cycle within the designated period.

A responsiveness test will be repeated once following a patient's failure to respond to a query cycle. If the patient fails to respond to the second test cycle, the system may go into a ramp down state as described earlier. Once patient responsiveness is regained, ART status section 78b (FIG. 15) may show a relevant message. Any automated ramp down of ESC, level, or infusion rate will continue, though, unless leveled off by the user in ramp down confirmation message 104 or the user changes the propofol dosage, ESC, level, or infusion rate as described below.

Figure 17:
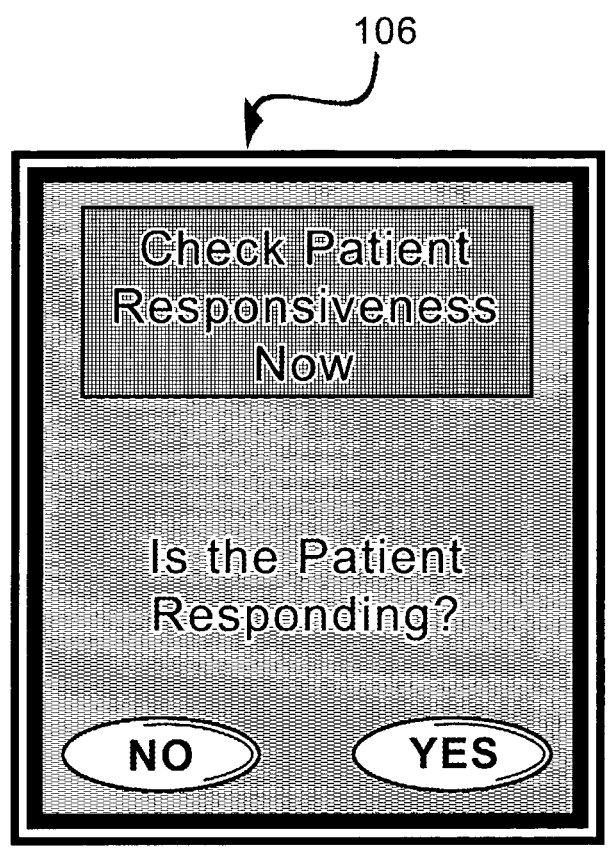
FIG. 17 shows an example display of a check responsiveness message according to one embodiment of the present invention

When the user selects the prompted manual ART option in the ART set-up preferences display, UI 1 prompts user 3 at the prescribed intervals with an audible indicator and a check responsiveness message window 106 (FIG. 17), displaying a relevant message in the ART status section 78b to alert user 3 to manually assess the patient's responsiveness. If user 3 does not respond to the UI's alert within a designated period of time or if user 3 responds that the patient is not responsive, UI 1 will remove the message and delivery system 2 will activate the ramp down state with confirmation procedure as described above. The response time for a failed manual ART query is shown in the ART history box 78a (FIG. 14) as a blue symbol at "15 s" when it actually exceeds 45 s. If user 3 responds that the patient is still responsive within 45 seconds, UI 1 will remove the message and delivery system 2 will continue the existing drug regime and the response is shown by a green symbol corresponding to "5" seconds even though the combined response time of the user and patient may be any time less than 45 seconds. This scheme takes into account that the response time of user 3, that is included in the total response time, may be variable, and that it will take longer to obtain a response when an intermediary is involved. A text message such as "Check patient" will be displayed in the ART status section 78b (FIG. 15), e.g., with white text on a green background as long as the prompted manual queries are responded to in the designated time period (e.g., 45 s) as indicated by a press of the "Yes" button in FIG. 17.

User 3 may disable automated administration of responsiveness tests by turning off the ART function by pressing the ART on/off button 56a on the membrane keypad 34 (FIG. 3). When the ART function is off, an appropriate indication or message will be shown in the ART status section 78b (FIG. 15). Responsiveness tests may still be initiated manually via the ART stat button 60 which will also turn the ART function on. If the user turns the ART function off while the system is still in a ramp down state because of the patient's failure to respond to a previous query or query cycle, the system continues the ramp down unless the user resets the drug level or selects to level off the drug ESC, infusion rate, or level.

Figure 18:
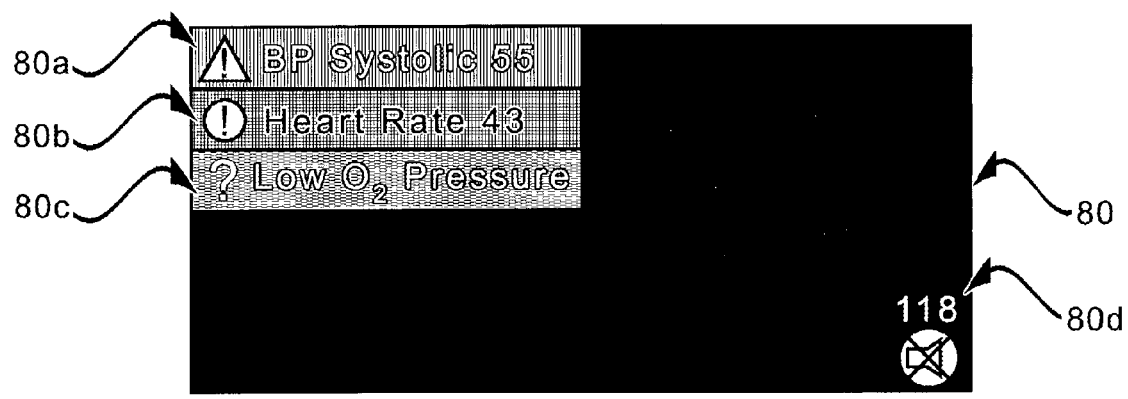
FIG. 18 shows an example display of a smart alarm box showing active alarms and advisories according to one embodiment of the present invention.

FIG. 18 shows an example of smart alarms box 80 which may display patient alarms and/or system advisories so that user 3 need only look to one location to quickly assess what alarms or advisories are present during a sedation and analgesia procedure. Additionally, smart alarms box 80 carries not only a label about which parameter (e.g., $SpO_2$) is alarming but also the complete information set, (e.g, $SpO_2$ 83) such that the user needs only look at one place to derive all the information relevant to the alarm state. When no alarms or advisories are present, smart alarm box 80 is colored a particular color (e.g., green). This background color is considered normal; the user need only glance at the box and see this color to know very quickly whether there are any alarms or advisories present. When, however, an alarm or system advisory is present, the background color of smart alarm box 80 turns to a different color (e.g., black) against which the alarm and/or advisory blocks stand out with greater contrast than the normal background color. The background of alarm and advisory blocks within smart alarm box 80 are themselves colored for emphasis (gray for advisories 80c, yellow for caution 80b and red for warning 80a) and are listed within alarm box in a priority as described below. When an active alarm is muted by the user (as described below), a mute symbol 80d will appear in a portion of smart alarm box 80. Muting an alarm does not affect the visual display of the remainder of smart alarm box 80 or the alarm and advisory blocks. FIG. 18 shows an example display of smart alarm box 80 with prioritized alarms and system advisories and a muted alarm symbol. To provide redundancy, in the event that a user may be color blind, a symbol is also presented next to each type of alarm (a white question mark "?" for advisories 80*c*, black circle on a yellow background with a black exclamation mark for cautions 80*b* and a white filled triangle with a black exclamation mark for warnings 80*a*).

Three levels of alarms may be provided with the system: system advisories, caution alarms, and warning alarms. The visual displays for these alarm levels may be color coded. For example, the displays of system advisories may be gray, caution alarms yellow, and warning alarms red. Color coding allows for a quick visual assessment of the meaning of an alarm display. A display of an alarm or advisory may be presented as a block within a column of other active alarm blocks taking up a portion of smart alarm box 80.

System advisories are presented to user 3 to alert him of current conditions about delivery system 2 that warrant present attention during a procedure. Advisories indicate user actions that may be needed (such as when remaining drug in a vial is low or a monitoring lead has come loose), but they do not necessarily result from an unusual patient state. Advisories may be presented to user 3 by a short and rapid audio tone and/or a visual display in smart alarm box 80. During the term of a system advisory, a block of smart alarm box 80 turns gray and a textual indication of the particular advisory is listed in that block. An icon or character, e.g., a question mark, may be shown next to the text message. An icon or character provides a redundant means for the user to delineate between advisories and alarms in addition to color color, this may be preferable for users who are color blind. The icon or character may flash. For added emphasis, the "flash" may change the size of the symbol in a "zooming" fashion. The audio tone sounds at regular intervals after the initiation of an advisory and continues at the same frequency until the problem leading to the advisory ceases or until the user suspends the alarms. The audio tone is presented at such a volume to be audible over ambient conditions The volume of the tone may be adjustable.

Delivery system conditions that warrant an advisory may be indicated to user 3 during a start-up diagnostics process. Advisory messages may be presented for, among others, the conditions listed in Table 5.1.

TABLE 5.1

System Advisories

| ADVISORY CONDITION | EXAMPLE ADVISORY MESSAGE |
|---|---|
| IV line occlusion: Vial Side | "Check IV - Vial" |
| IV line occulsion: Pump Side | "Check IV - Pump" |
| Vial empty | "Vial Empty" |
| Vial near empty | "Low Vial" |
| Pump fault | "Pump Fault" |
| NIBP weak signal | "NIBP weak" |
| NIBP erratic signal | "NIBP Error" |
| NIBP retry limit exceeded | "NIBP Error" |
| NIBP measurement timeout | "NIBP Timeout" |
| NIBP blocked valve | "NIBP Valve" |
| NIBP air leak | "NIBP Leak" |
| NIBP safety timeout | "NIBP Timeout" |
| NIBP cuff overpressure | "NIBP Press" |
| NIBP fault | "NIBP Error" |
| Printer paper out | "Add Paper" |
| Printer fault | "Print Error" |
| Capnometer occlusion | "Cap Block" |
| Capnometer fault | "Cap Error" |
| ECG fault | "ECG Error" |
| ECG lead failure | "ECG Lead Error" |

TABLE 5.1-continued

System Advisories

| ADVISORY CONDITION | EXAMPLE ADVISORY MESSAGE |
|---|---|
| $CpO_2$ fault | "$SpO_2$ Error" |
| $SpO_2$ probe failure | "$SpO_2$ Probe Error" |
| $SpO_2$ no sensor | "$SpO_2$ Sensor" |
| $SpO_2$ low perfusion | "$SpO_2$ Low" |
| $SpO_2$ Searching | "$SpO_2$ ?" |
| $SpO_2$ Interference detected | "$SpO_2$ Block" |
| $SpO_2$ sensor not on patient | "$SpO_2$ Connect" |
| $SpO_2$ high ambient light | "$SpO_2$ Bright" |
| $SpO_2$ invalid sensor | "$SpO_2$ Sensor" |
| Low $O_2$ source pressure | "Low $O_2$ Press" |
| High $O_2$ source pressure | "Hi $O_2$ Press" |
| Cabinet temperature high | "System Temp High" |
| Loss of A/C mains | "A/C Power Lost" |
| Air in line | "Air in line" |
| Invalid Vial | "Invalid Vial" |
| Invalid Cassette | "Invalid Cassette" |
| Air in Line | "Air in Line" |
| Incorrect $O_2$ Gas Mixture | "Incorrect $O_2$ Gas Mixture" |

Caution or warning alarms may be presented to user 3 whenever a patient state parameter exceeds a designated alarm limit or range for either caution or warning states. Caution and warning alarms may be indicated to user 3 by a continuous audio tone or sequence of tones. The audio tone is presented at such a volume to be audible over ambient conditions. The volume of the tone may be adjustable. During the term of a caution or warning alarm, a background block of smart alarm box 80 turns a particular color (e.g., yellow for caution or red for warning) and a text message regarding the alarm will be listed in that block in letters colored so as to be easily visible over the background color (e.g., black text on yellow background for a caution alarm or white text on a red background for a warning alarm). An icon or character, may be shown next to the text message. An icon or character provides a redundant means for the user to delineate between advisories and alarms other than by color; this is preferable for users who are color blind. The icon or character may flash. For added emphasis, the "flash" may change the size of the symbol in a "zooming" fashion.

During the term of a caution or warning alarm, the alarming parameter may be displayed along with the current value of the parameter in the corresponding parameter data box 82 on primary monitoring display 70 (FIG. 5). The background color of the data box also changes to the color of the alarm (e.g., yellow for caution or red for warning) and the current value for the alarming parameter is displayed in a color easily read against the alarming background color The current value for an alarming parameter may be continuously updated and displayed for as long as the alarm condition is present. FIG. 9, described above, shows an example of a parameter box 300 with caution and warning alarms active for two parameters.

An alarm sounds and displays continuously until the alarming condition ceases, until the user acts by pressing mute alarms button 13 or the suspend alarms 11 button on membrane keypad 34 (FIG. 3) for some alarms, or until the alarm settings are reset. A muted alarm is reinstated after the specified mute period if the problem causing the alarm has not ceased. Visual display of an alarm is not affected by an audio mute. After an alarm clears, an audio tone for a cleared alarm sounds and the visual display of the alarm message changes to the normal color scheme (e.g., white letters on a black background). The visual display persists for a short period of time without the zooming flash of a symbol. The parameter value is replaced for a limited period of time by a message indicative of a cleared alarm (e.g., "OK"). When no alarms are displayed, smart alarm box 80 returns to its normal background color (e.g., green).

Caution or warning alarms for low $SpO_2$, low heart rate, low blood pressure, or low respiration may prompt delivery system 2 to administer a new ART query, if responsiveness testing is enabled, for each new alarm. Caution or warning alarms for low or high blood pressure (systolic, diastolic or mean arterial pressure) may prompt delivery system 2 to cause a new blood pressure reading to be taken once for each new alarm. Caution or warning alarms for low $SpO_2$, or low or high heart rate may prompt delivery system 2 to cause a new blood pressure reading to be taken once for each new alarm, if the NIBP monitor is activated.

Caution alarms for low $SpO_2$ or respiration rate may prompt delivery system 2 to immediately decrease propofol drug administration or ESC to a fraction of its current level. Upon automated drug reduction, delivery system 2 presents a drug decrease over-ride screen for a limited period of time during which user 3 may over-ride the delivery system's automated drug reduction action by touching an appropriate button. If user 3 selects the over-ride button an over-ride confirmation screen will be displayed. From the confirmation screen, user 3 is presented buttons for activating the following options: resume the administration of propofol at the pre-alarm level; or cancel the over-ride allowing the system's automated propofol reduction to continue. If user 3 selects to resume administration, delivery system 2 will bring its effect site concentration, infusion rate, or level back to the pre-alarm level as the automated reduction will have taken effect in the interim between the alarm and the time the user selects the resume function.

If $SpO_2$ low caution or respiration rate low caution alarms continue to exist after a certain period of time has passed (e.g., 4 minutes) following a first automated propofol reduction, the system will automatically reduce propofol again, using this same procedure described above. A user-override of the system's automated propofol reduction stays in effect for the duration of the affected alarm, i.e., delivery system 2 does not attempt to reduce propofol a second time in response to the same alarmed state.

Warning alarms for low $SpO_2$ or respiration rate prompt delivery system 2 to immediately stop drug administration. Upon the ceasing of drug administration, delivery system 2 presents a stop drugs over-ride screen for a limited period of time during which user 3 may over-ride the system's automated drug cessation. If user 3 selects the over-ride button an over-ride confirmation screen will be displayed. From the confirmation screen, user 3 is presented buttons for activating the following options: resume the administration of propofol at the pre-alarm level; or cancel the over-ride allowing the system's automated propofol cessation procedure to continue. If user 3 selects to resume administration, delivery system 2 will bring its effect site concentration, infusion rate, or level back to the pre-alarm level as the automated cessation will have taken effect in the interim between the alarm and the time user 3 selects the resume function.

A user-override of the system's automated propofol cessation stays in effect for the duration of the affected alarm, i.e., delivery system 2 does not attempt to stop propofol administration a second time in response to the same alarmed state.

Still referring to FIG. 18, when multiple alarms and/or system advisories are present, delivery system 2 presents user 3 with the audio tone indicative of the highest priority audio alarm. The visual displays of the alarms and/or advisories are listed in the smart alarm box 80 on primary monitoring display 70 in their order of priority from highest to lowest. In one embodiment of the present invention, the alarms and advisories are prioritized as follows: warning, caution, advisory, and then cleared alarms. Within each of these categories, the alarms or advisories are prioritized by the order of their occurrence with the most recent being the highest priority. UI 1 displays the alarms and advisories as within blocks of the smart alarm box 80 from top-to-bottom in a column where the highest priority message is displayed at the top of the column. When more than one column is needed within smart alarm box 80 to display many messages, the highest priority messages are displayed in the leftmost column. Each alarm message and appropriate symbology or icon is presented in the appropriate color and against the appropriate background color as described above with the remaining portion of smart alarm box 80 not containing alarm messages being displayed in a color different from normal and different from the alarm background colors (black for example). FIG. 18 shows an example display of smart alarm box 80 containing prioritized alarm and advisory blocks.

Mute alarms button 13 provided on membrane keypad (FIG. 3), when touched, will cause the audio signal of a current alarm to be muted. The muting occurs for a particular period of time and may be extended upon subsequent touching of mute alarms button 13 up to a particular maximum mute time limit. By one example, pressing the button once mutes the alarm for 60 seconds, pressing it again before the first 60 seconds have expired will add another 60 seconds to the mute time countdown and pressing it each time will add another 60 seconds up to a total mute time countdown of 180 seconds. The time remaining in the mute period is displayed so that user 3 may anticipate the recurrence of alarm sounds so as to be able to preempt such recurrence by pressing the button again to timely extend the mute period. The maximum mute time limit assures that user 3 acknowledges the currency of alarms by forcing him to take proactive steps at least every so often, e.g., 180 s, to continue working without audible alarms.

A new alarm occurring during a mute period will end the current mute period thereby causing the presentation of audio and visual signals for the new alarm. Pressing mute alarm button 13 after such a new alarm will begin a new mute period. The current mute period and the displayed time remaining in it apply to all current alarms.

Figure 19:
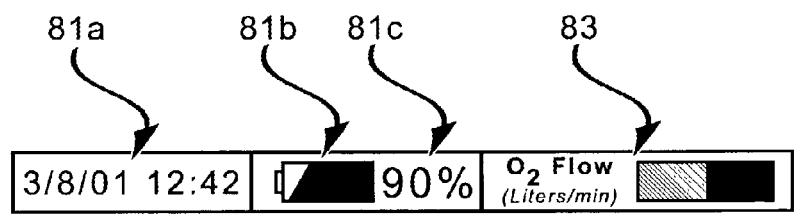
FIG. 19 shows an example display of a section of a monitoring display containing clock, date, and power status information, and a thermometer bar depicting $O_2$ flow.

FIG. 19 shows an example display of a bar 83 containing time, date, and power status information. The date and time of day 81*a* may be displayed within another portion of the display bar 83; both are settable by user 3 from the system information display described below. An icon 81*b* may also be displayed which indicates the current charge level of the system's battery. A percentage value of the level of charge 81*c* may also be shown. Alternatively, or in addition, a time value indicating how long the system may be run on the remaining battery charge may be displayed. These battery indications may be colored differently when the system is operating on battery power than when it is operating on external electrical current.

The current level (e.g., none, low, medium, or high) of supplemental $O_2$ being provided to a patient may also be shown in a status box 83. This information may be shown graphically as a horizontal thermometer bar or textually as a value representing $O_2$ flow. FIG. 19 also shows an example display of a thermometer bar depicting $O_2$ flow at a medium rate.

Figure 20:
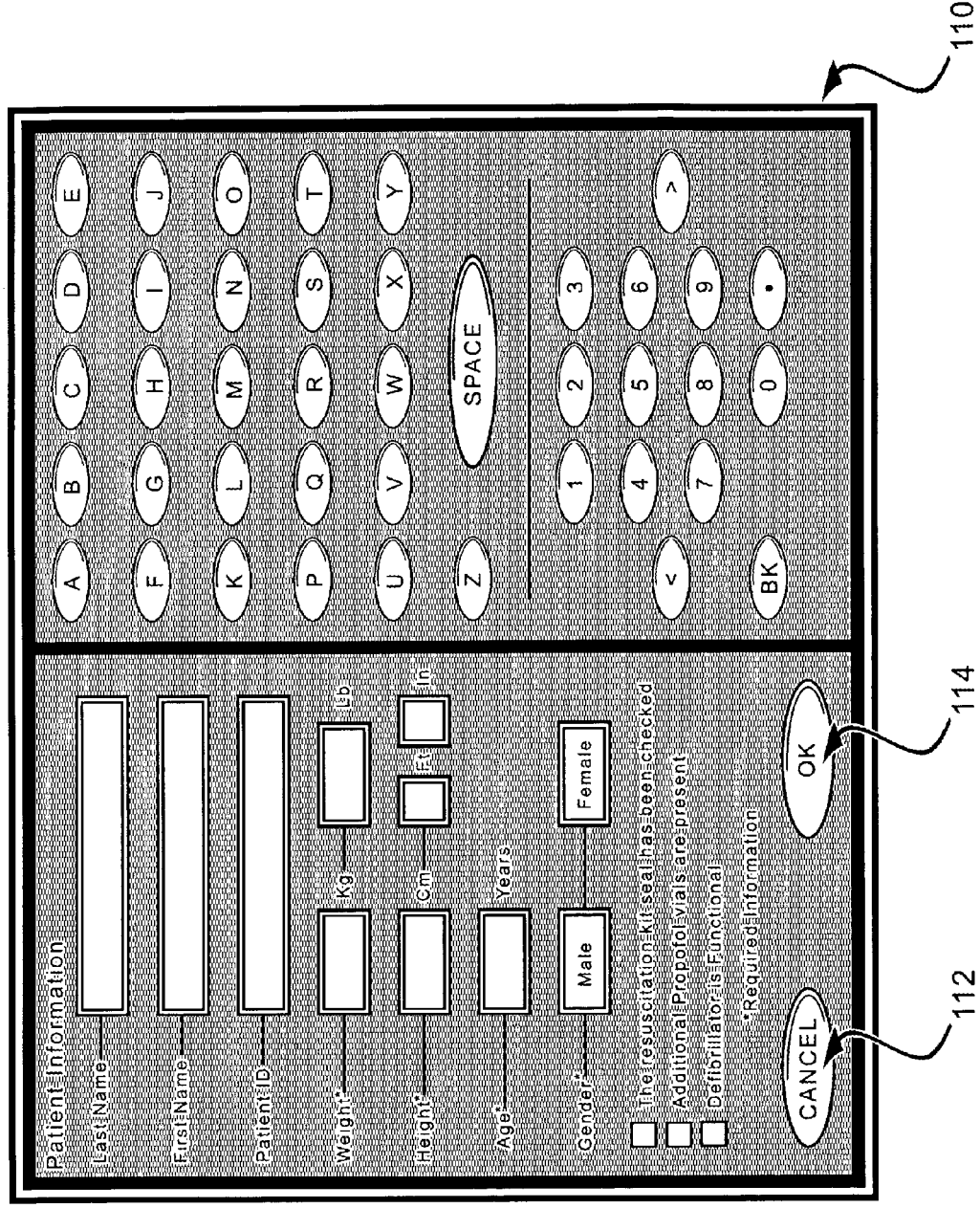
FIG. 20 shows an example of a patient information display according to one embodiment of the present invention.

FIG. 20 shows an example display of a patient information display 110. Patient information display 110 may provide data entry boxes for the entry of patient weight, height, age and gender. The patient name and identification may also be part of the entered data. Weight, height, age, and gender information are used by the target control infusion algorithm of the system to calculate propofol effect-site concentration information. Data can be entered into this screen by touching the appropriate text entry box and entering the associated information via the membrane keypad or the touch screen keypad. The weight and height information may be entered in either kg or lb. and the height information may be entered in cm or feet and inches. Entry of information in the kg box causes the calculated conversion to appear in the lb. box, and vice-versa. Entry of information in the cm box causes the calculated conversion to appear in the feet and inches boxes and vice-versa. The Male/Female boxes toggle with neither selected as a default. These entry conveniences add a layer of certainty to the values the user enters for the patient information because they require the user to contemplate what value is being entered. The lack of defaults displayed in the parameter fields ensures that no erroneous value is used by the system merely because it is the default value that a user neglected to change.

Figure 21:
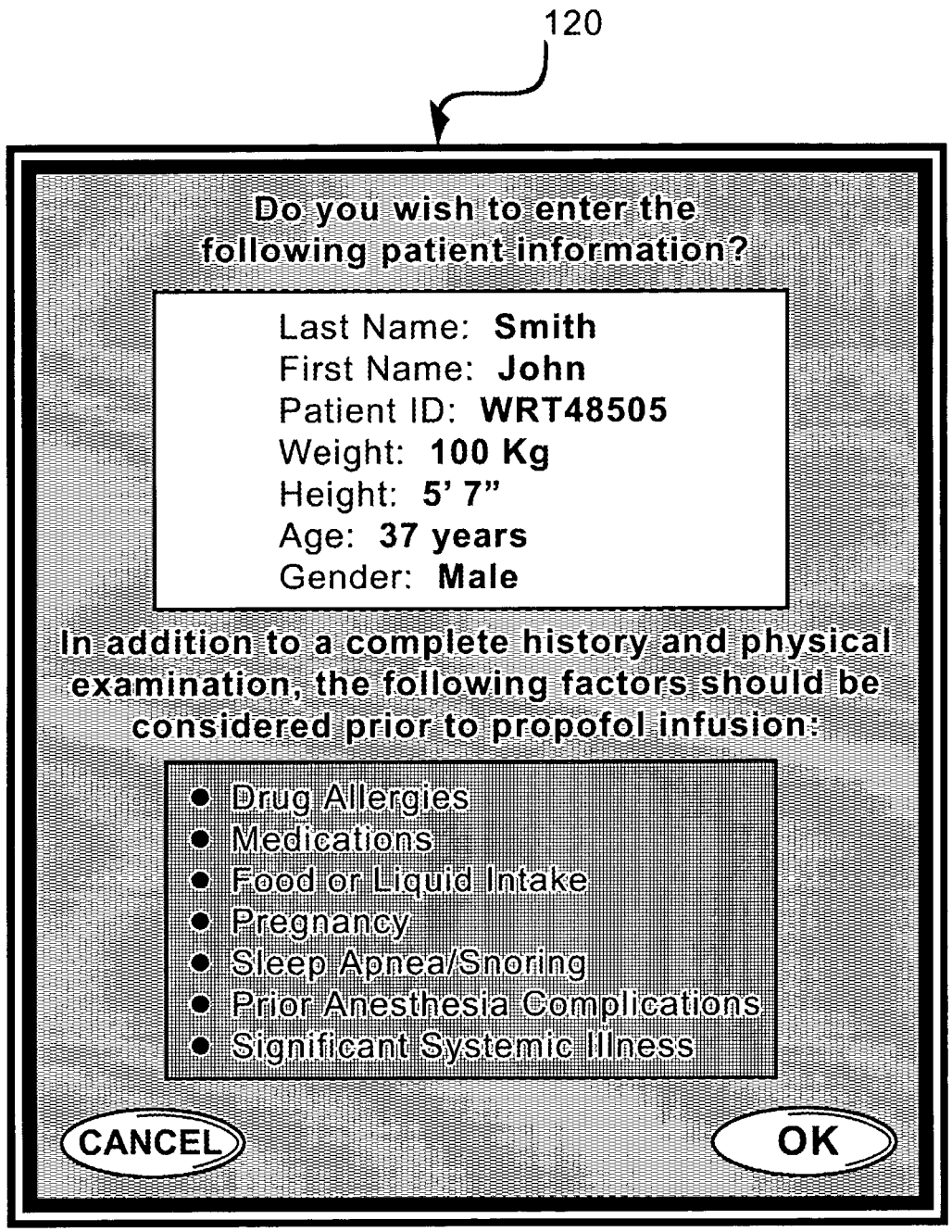
FIG. 21 shows an example of a patient data entry confirmation display according to one embodiment of the present invention.

Patient information display 110 may be accessed by user 3 by touching a Patient Info Button on the membrane keypad 34 (FIG. 3) and may be presented as a pop-up window over primary monitoring display 70. Upon commencement of sedation and analgesia to a given patient, patient information display 110 may not be modified; instead, a user touching patient info button 17 (FIG. 3) during a sedation and analgesia procedure will be presented with a pop-up window 120 reporting the current patient data (FIG. 21).

As an additional layer of security against gross mis-entry of data, delivery system 2 uses weight nomograms that correlate entered weight to entered height, age and gender to catch incorrect entries. This is especially important because the drug infusion may often be calculated on the basis of the entered weight and mis-entry of patient weight by the user may have serious consequences. Delivery system 2 references these nomograms to perform certain checks on the patient information entered by the user and prompt the user to confirm any entries that are inconsistent with the nomogram checks in order to catch obvious errors in the entry. For example, if a user enters a value for a patient's age as two years and a value for the same patient's weight as 300 pounds, then the system software would prompt the user for additional confirmation of his entry before proceeding. If, however, the user's entries check out by the software, then the system will proceed to the next step in the initiation of a new procedure. As an added security measure, the units of height and weight are displayed in at least two sets of commonly used units to prevent mis-entry based on confusion between units. Weight can be entered in either kg or pounds and is displayed in both units irrespective of which weight units entry field is used. Height can be entered in either cm or feet and inches and is displayed in both units irrespective of which height units entry field is used.

Certain checkboxes including a checkbox indicating that the user has checked a tamper-proof seal on a resuscitation kit, a checkbox indicating that the user has checked for the presence of and proper functionality of a resuscitation defibrillator, and a checkbox indicating that the user has obtained additional propofol vials must be checked by the user before the entry of patient information will be considered complete by the system. The checkbox for the defibrillator may be omitted in UI 1 if the defibrillator is stored in the resuscitation kit. An unbroken seal on a resuscitation kit indicates to the user that the resuscitation kit has not been used since it was last restocked or certified, giving the user and the patient assurance that the needed emergency supplies will be at hand and functional if needed. This pre-use check sequence requires the user to make certain that prerequisite conditions have been met before the system will initiate administration of sedatives or potent drugs to the patient. Reminding users to perform these or other actions serves as a redundant means of assuring that inexperience or lack of recency in delivering sedation and analgesia does not jeopardize patient safety.

Referring again to FIG. 20, touching cancel button 112 during patient data entry negates the transaction and returns the patient information to any previously stored values. Touching an OK button 114 will cause the system to check to insure that the data entered is complete and valid. If the patient information is not complete, a patient data error message is displayed and the user may be prompted to enter complete information. Particular recommended limits are provided with the system for each of height, age, and weight. If the patient information entered by a user exceeds these recommended limits, a patient data warning message is displayed, that allows the user to change an entry by going back to patient information display 110.

FIG. 21 shows an example display of patient data entry confirmation display 120. Once the data entered is complete and checked for validity by delivery system 2, patient data entry confirmation display 120 will be presented to the user to confirm his intentions. Requiring user 3 to confirm data once entered allows him to possibly catch mistakes in entry thereby reducing the risk of patient harm due to user entry errors. Also on patient data entry confirmation display 120 or on a separate screen, user 3 may be reminded of certain factors to be considered about the patient before commencing sedation and analgesia. Reminding user 3 of critical elements of a complete history and physical examination that relate directly to risks associated with sedation and analgesia prior to the initiation of drug administration allows the user to catch situations that may pose problems with sedating the patient using the current set-up prior to initiating propofol administration.

Figure 22:
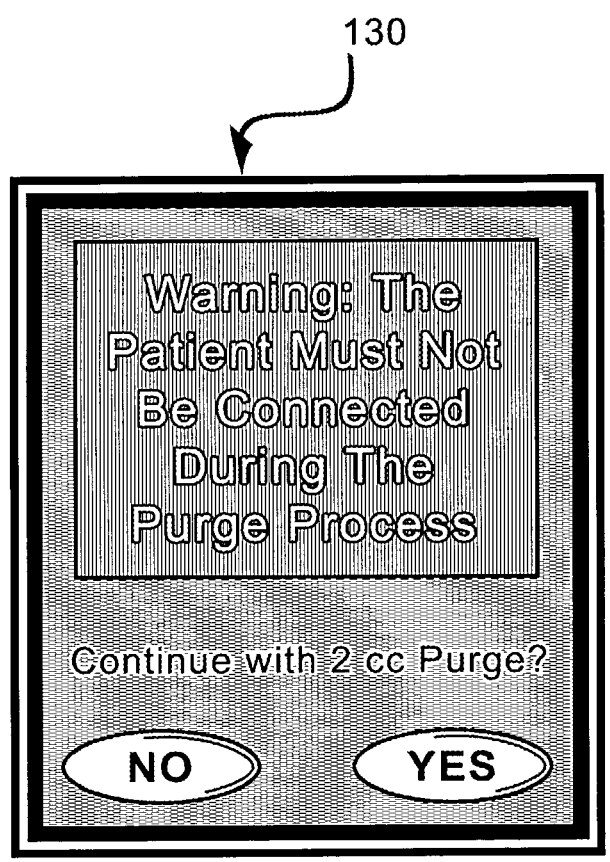
FIG. 22 shows an example of a purge IV set confirmation display according to one embodiment of the present invention.

FIG. 22 shows an example of propofol purge IV set confirmation display 130. Upon user 3 pressing purge IV set button 51 on membrane keypad 34 (FIG. 3) and upon certain precursor conditions being met, propofol purge IV set confirmation display 130 is presented to user 3. These precursor conditions may include the presence of a valid drug cassette properly loaded into position with the housing of delivery system 2 and the presence of a valid propofol vial properly loaded into position with the cassette. If these precursor conditions are not met when user 3 seeks to activate the purge IV set function, UI 1 displays an appropriate error message. Propofol purge IV set confirmation display 130 reminds user 3 that the patient must not be connected to the infusion system during a purge process Delivery system 2 only proceeds with a purge sequence if user 3 has been presented this reminder and subsequently indicates that he wants to proceed with the purge sequence. Pressing purge IV set button 51 allows user 3 to initiate a purge sequence by taking just two quick actions: a hard key press followed by confirmation via a touch button. Delivery system 2 then automatically purges the IV set with a pre-selected and empirically determined volume of drug upon that single act by user 3. The drug volume extracted from the drug container for priming or purging is not added to the amount of drug administered to the patient that is calculated by the drug control model but is added to the total volume extracted from the container as part of the algorithm to calculate the remaining drug volume and predict drug container exhaustion.

Delivery system 2 also ensures that certain precursor conditions are met prior to propofol administration to a patient connected to the infusion system. Upon user 1 seeking to activate the normal or stat propofol administration functions, delivery system 2 will check to ensure that these precursor conditions are met. The requisite precursor conditions for the initial activation of any of the three drug delivery modes may include: entered and confirmed requisite patient data, confirmation that the resuscitation kit seal is present and intact, the presence of a valid cassette properly loaded into position, the presence of a valid vial properly loaded into position, the presence of main A/C power, the presence of at least an 80% system battery charge, the confirmation of the presence of a functional defibrillator, that at least one purge of the infusion line has been done prior to the procedure, that no air-in-line indication is detected by the IV pump, and the presence of at least one of the following signals: respiratory rate, SpO2 and heart rate. If any of the precursor conditions are not met, delivery system 2 will not initiate administration and will display a propofol administration error message to user 3 containing a description of the specific conditions that have not been satisfied. An error tone may also be played.

Figure 23:
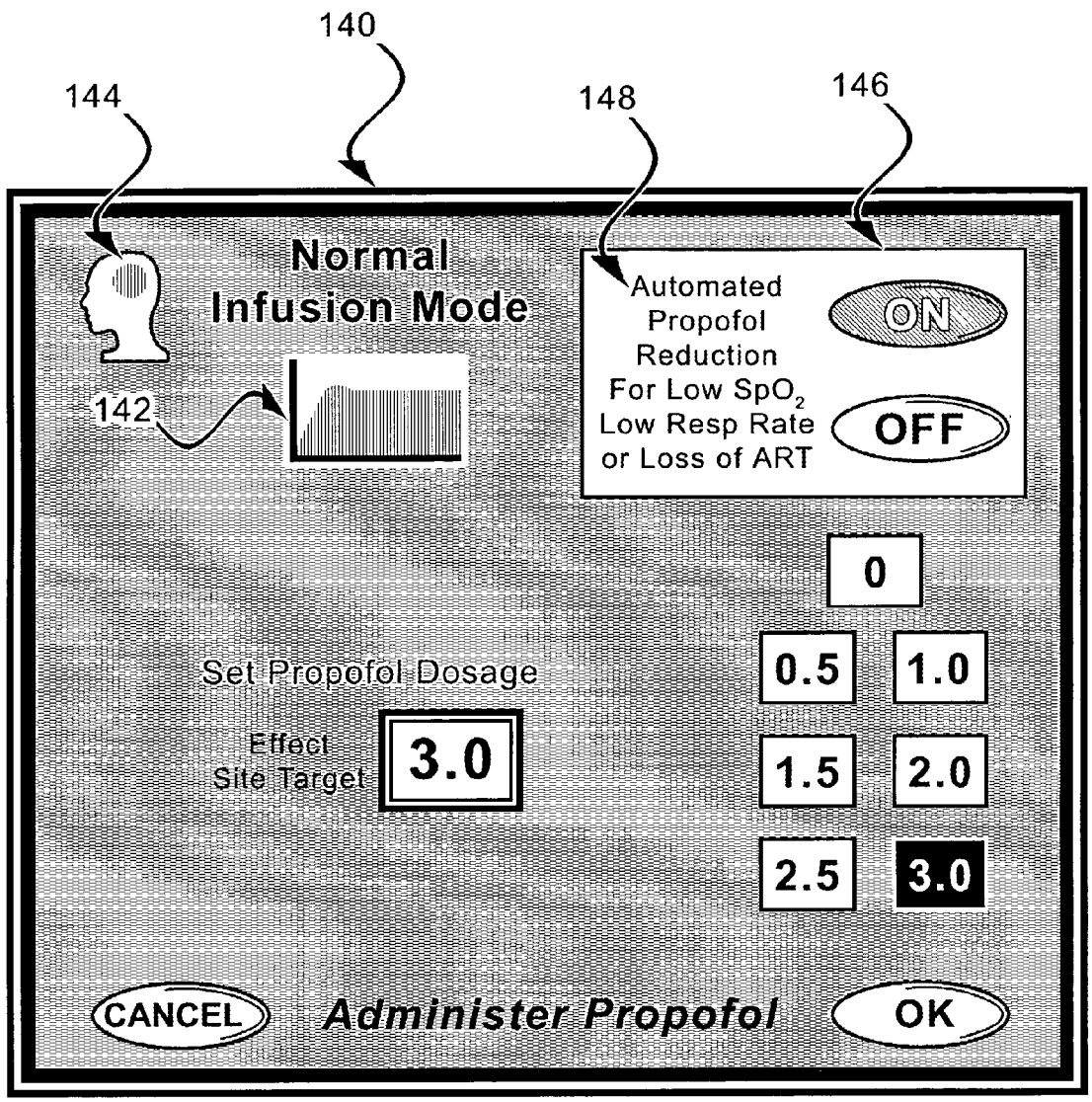
FIG. 23 shows an example of a normal mode dosage display according to one embodiment of the present invention.

FIG. 23 shows an example of normal mode dosage display 140. User 3 may initiate a steady ramp-up of propofol to a targeted effect-site concentration (ESC), infusion rate, or level by activating the normal mode key 47 in the propofol portion of the membrane keypad 34 (FIG. 3). Upon activation of this key, normal mode dosage display 140 is presented to user 3. For example, within this display, the current ESC of propofol chosen or being currently administered is shown in a touch entry data box. A default ESC, infusion rate or dose of zero may be shown in a touch entry data box. A new ESC, infusion rate or dose level can be entered by the user via a keypad or through buttons on the normal mode dosage display that represent several typically chosen ESCs, infusion rates, or dosages. The normal mode dosage display may also include a graphical depiction 142 of the projected ESC or dose. The iconic depictions 142 of the drug infusion modes may resemble the projected graph of ESC or dose displayed in the propofol infusion box 76 within the monitoring display 70 such that the user can easily recognize what the drug infusion mode is meant to achieve and how it will achieve it. An icon 144 depicting the effect-site (e.g., a colored symbol shown inside the outline of a human head where the effect-site is located at the patient's brain) may also be included on normal mode dosage display 140 to remind user 3 or reinforce his knowledge that the values for propofol given on the screen relate to the effect-site concentration. A box 146 may also be included in the dosage display which allows the user to turn on/off the automated propofol reduction feature in which the system reduces ESC, infusion rate or dosage upon low parameter values for SpO$_2$ or respiratory rate (described below) or for a slow or failed response to an ART (described above). Box 146 includes a sufficient message 148 to inform the user why the automated reduction would kick in if the function is active.

Figure 24:
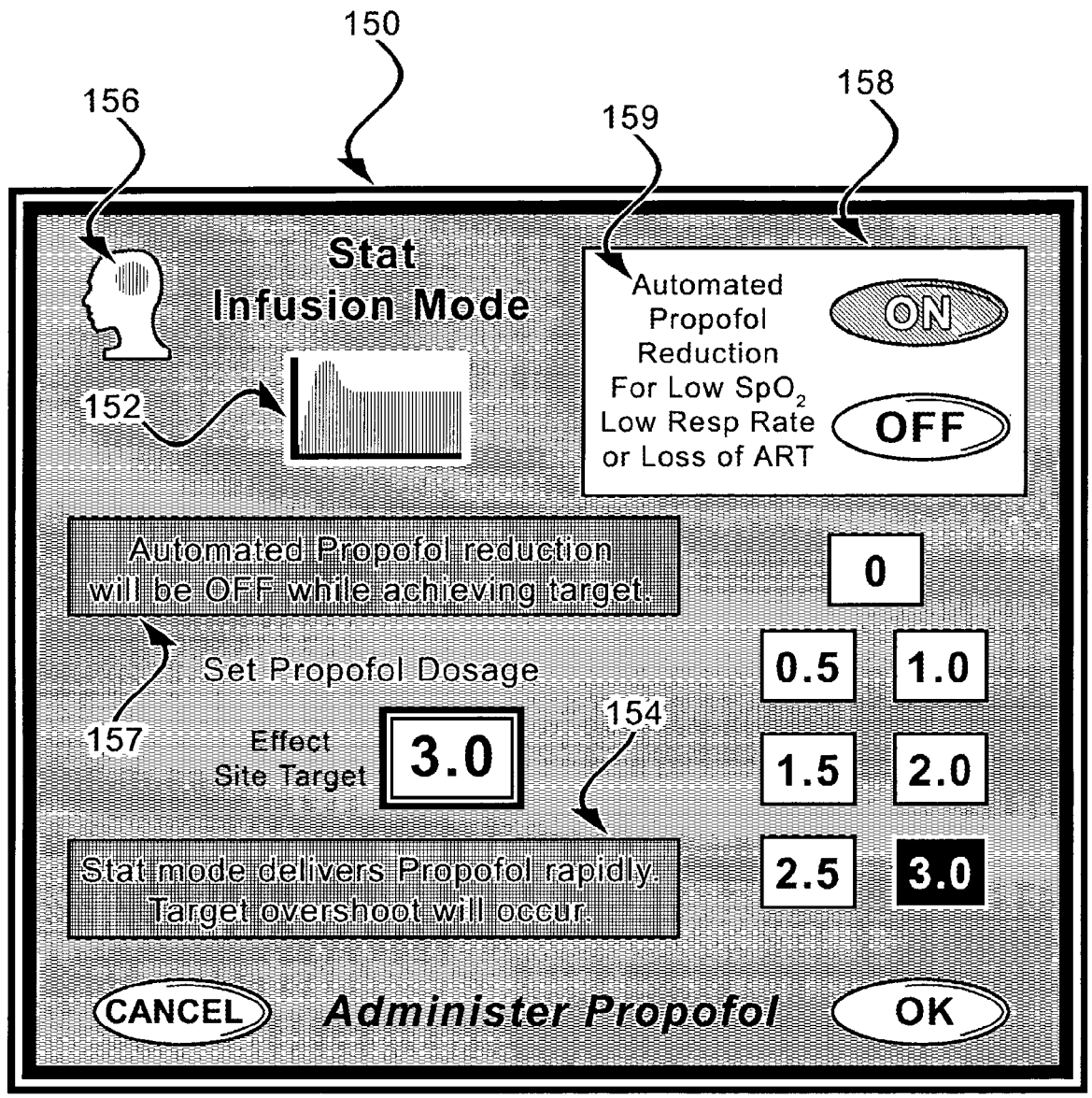
FIG. 24 shows an example of a stat mode dosage display according to one embodiment of the present invention.

FIG. 24 shows an example display of stat mode dosage display 150. User 3 may also initiate a provision of propofol at a rate that will allow a targeted ESC or dosage to be reached as quickly as possible by activating the stat mode key 49 in the propofol portion 46 of the membrane keypad 34 (an overshoot of the targeted ESC is possible with this administration mode). Upon activation of this key, stat mode dosage display 150 is presented to user 3. Within this display, the current ESC, infusion rate or dose of propofol chosen or being currently administered is shown in a touch entry data box. A default ESC or dose of zero may be shown in a touch entry data box. A new concentration can be entered by the user via a keypad or through buttons on the stat mode dosage display 150 that represent several typically chosen ESCs or doses. Stat mode dosage display 150 may also include a graphical depiction 152 of the projected effect-site level. This depiction 152 may resemble the projected graph of effect-site level displayed in propofol infusion box 76 (FIG. 5) such that user 3 can easily recognize what the stat mode drug state is meant to achieve and how it will achieve it. This graphical depiction 152 may include a hump representing the possible overshoot of the targeted ESC. Further, a text message box 154 may also be included on stat mode dosage display 150 to alert user 3 of possible overshoot. With such representations, user 3 is reminded that the stat mode may cause an overshoot. An icon 156 depicting the effect-site (e.g., a colored symbol shown inside the outline of a human head where the effect-site location is at the patient's brain) may also be included on stat mode dosage display 150 to remind user 3 or reinforce his knowledge that the values for propofol given on the screen relate to the effect-site concentration. A box 158 may also be included in the dosage display which allows user 3 to turn on/off the automated propofol reduction feature in which delivery system 2 reduces ESC or dose upon low parameter values for SpO$_2$ or respiratory rate (described below) or for a slow or failed response to an ART (described above). This box includes a sufficient message 159 to inform user 3 why the automated reduction would kick in if the function is active The automated propofol ESC or dose reduction feature will be switched off by delivery system 2, however, while the stat mode is achieving the target ESC or dose. An appropriate text message box 157 is included on stat mode dosage display 150 to alert user 3 of this action by delivery system 2 before this action is taken and while this action is being taken.

Figure 25:
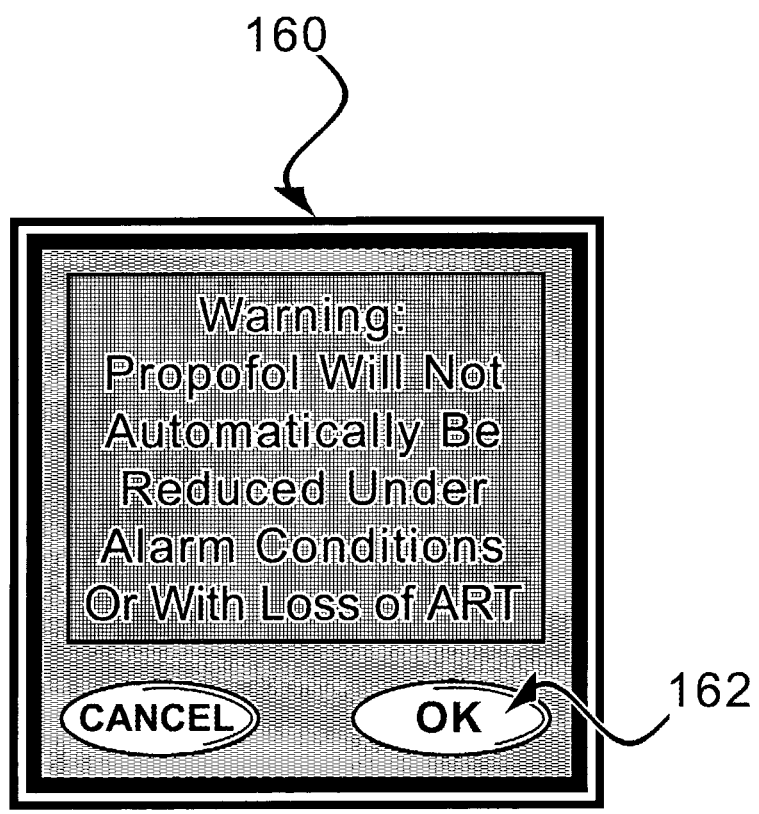
FIG. 25 shows example displays of drug warning screens according to one embodiment of the present invention.

FIG. 25 shows an example display of automated propofol reduction off confirmation screen 160. If user 3 disables the automated reduction feature from either dosage display, UI 1 will present him with automated propofol reduction off confirmation screen 160 overlaid on the dosage screen. Upon user 3 touching an OK button 162 on the confirmation screen, delivery system 2 proceeds with disabling the automated propofol reduction. Once disabled, automatic propofol reduction will remain disabled until user 3 re-enables it by navigating the same screens described above. During periods where the automated propofol reduction is disabled, a message to that effect may be displayed in a portion of smart alarm box 80 (FIG. 5) such that user 3 is always alerted to the fact that the default automated propofol reduction feature is inactive. UI 1 continuously warns user 3 when significant changes to the delivery system's safety algorithms and data set have been made as well as requiring user confirmation before such changes are made. A similar message may also be displayed to user 3 during a period of propofol ESC or level increase when delivery system 2 is administering drugs in the stat delivery mode, even if the automated reduction feature is active because delivery system 2 will temporarily not use the feature while such ESC or level increase is proceeding. In both the stat and normal modes, when user 3 selects a new target effect-site concentration of propofol and then confirms the new ESC target, UI 1 updates the future projection of the ESC and displays it in the projected target effect-site graph 76b of the propofol infusion box 76 (described above with respect to FIG. 12). The actual change in the propofol ESC that delivery system 2 administers to the patient is only initiated upon user 3 touching an OK button on the respective dosage mode display. Delivery system 2 does not change the current propofol ESC administered to the patient if the user touches a cancel button on the respective dosage mode display.

Figure 26:
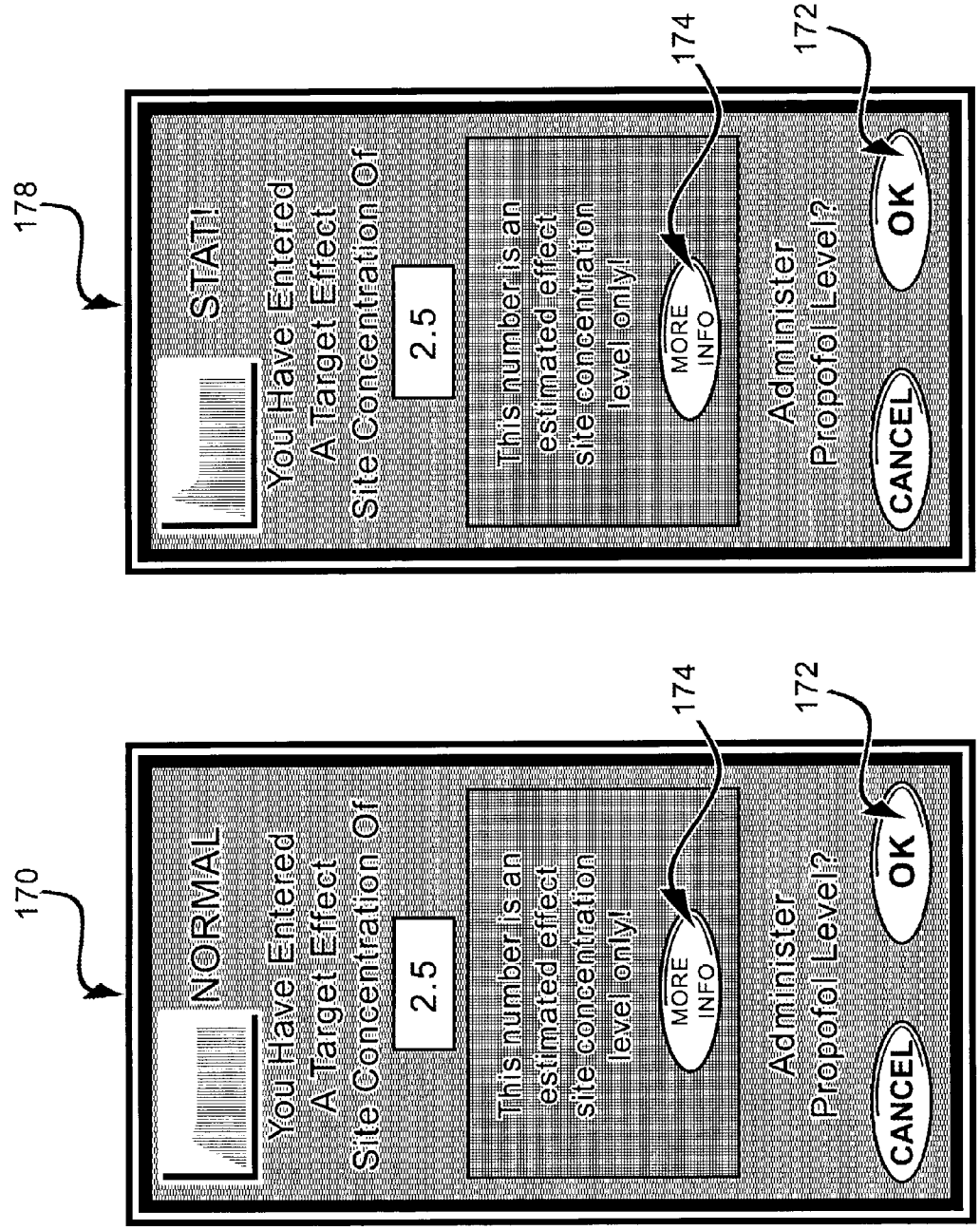
FIG. 26 shows example displays of normal mode and stat mode confirmation screens according to one embodiment of the present invention.

FIG. 26 shows example displays of normal mode 170 and stat mode 178 confirmation screens. An intermediate display 170 may be presented to user 3 prior to the change, though, in order to have user 3 confirm his understanding that the propofol ESC entered is a target effect-site level only. When such an embodiment is implemented, delivery system 2 only changes the current propofol ESC upon user 3 touching an OK button 172 on normal mode confirmation screen 170. These confirmation screens may be specific to each of the normal and stat modes of delivery and may include a button 174 that when touched will activate another display that remonds user 3 of the theory and assumptions behind effect-site control of propofol levels They may also re-display the user's chosen ESC so as to give him a chance to cancel the change if he then realizes that the entered value was in error.

Figure 27:
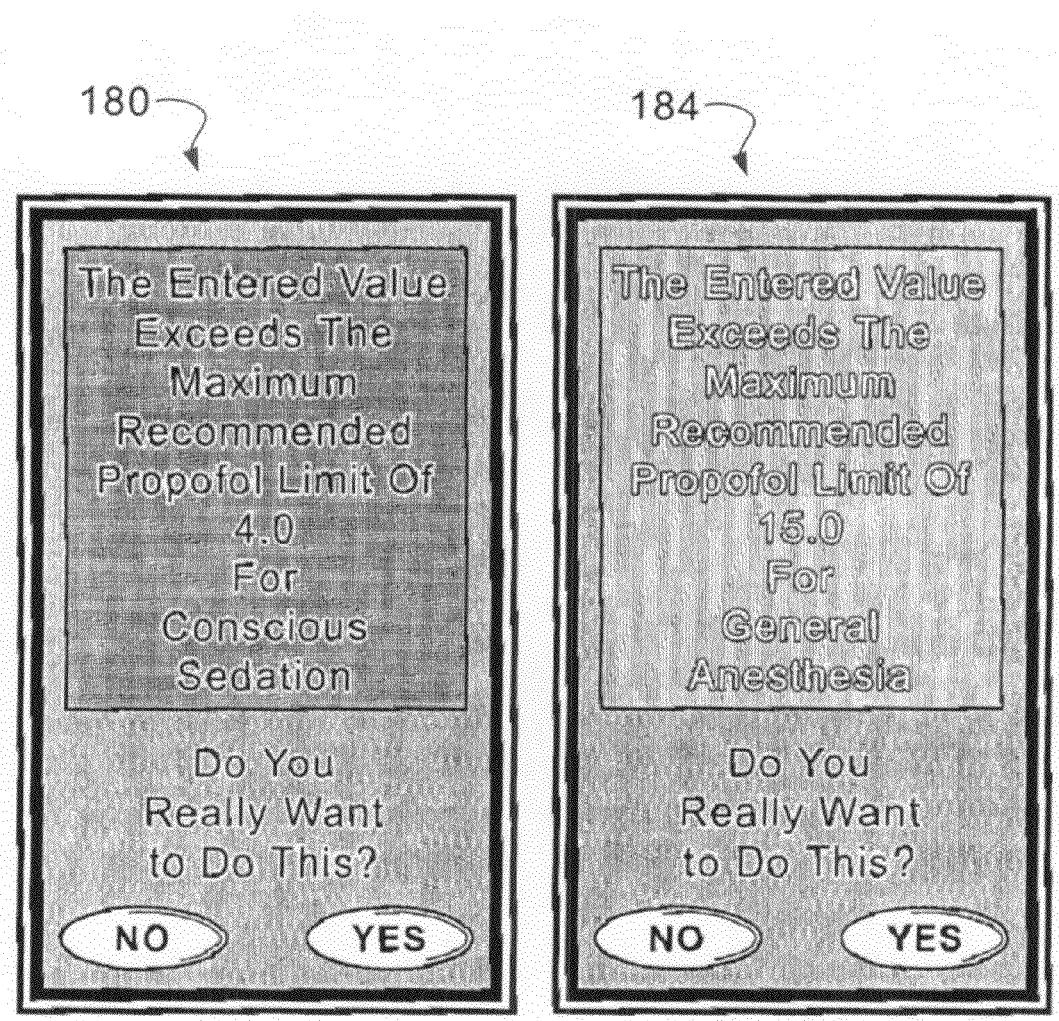
FIG. 27 shows an example display of an automated propofol reduction off confirmation screen according to one embodiment of the present invention.

FIG. 27 shows example displays of drug caution and warning screens 180 and 184. Delivery system 2 recognizes certain ranges of values for user entered levels, doses, infusion rates or effect-site concentrations for which it may require additional confirmation by the user before targeting. These values are represented in a safety-data set stored within the system's memory. For example, if the user-entered ESC is less than a particular value in the safety data set proportionate to the patient's age (e.g., 4.0 □g/cc for patients younger than 70 or 3.0 □g/cc for patients 70 or older), delivery system 2 will proceed with the initiation process for propofol administration, i.e., it will change the current level administered or it will display the systems initiation screen (described below) at the beginning of a new procedure. For example, if the user-entered ESC exceeds that particular value, but is less than a second value (e.g., 15 □g/cc), UI 1 will display drug warning screen for sedation and analgesia 180 to user 3, which cautions user 3 that the value he entered exceeds the maximum recommended propofol limit for sedation and analgesia. This screen will prompt user 3 to confirm or cancel his intention to achieve the entered ESC. It may include a color background for the text representative of the caution (e.g., yellow). For example, if the user-entered ESC exceeds the second value but is still less than a third value (e.g., 20 □g/cc), the system will display drug warning screen for general anesthesia 184 to user 3, which warns him that the value he entered exceeds the maximum recommended propofol limit for general anesthesia. This screen will prompt user 3 to confirm or cancel his intention to achieve the entered ESC. It may include a color background for the text representative of the warning (e.g., red). Upon user 3 confirming his entered level at one of these warning screens, delivery system 2 will change the current level administered or UI 1 will display the systems initiation screen (described below) at the beginning of a new procedure. If user 3 entered ESC exceeds even the third value, UI 1 will display a propofol exceedance error message to user 3, will return to displaying the dosage mode screen, and the delivery system 2 will not allow the initiation of propofol administration until a new and lower ESC value is entered by user 3. These value checking and redundant confirmation features of the system may significantly reduce the risk that inadvertent entries by user 3 will go unnoticed to the point of delivery system 2 administering a propofol level sufficient to cause patient overdose.

Once the appropriate user confirmations have been made, UI 1 will return to the primary monitoring display 70, and the flow indicator 76e in the propofol target level box and the propofol LEDs 48 on keypad 34 (FIG. 3) will begin to move or light at the prescribed sequence and rate. User 3 may discontinue propofol administration at any time by navigating through the above screens and entering an effect-site level of zero, or by pressing stop propofol button 53 located within the propofol portion 46 of the membrane keypad 34 (FIG. 3).

Figure 28:
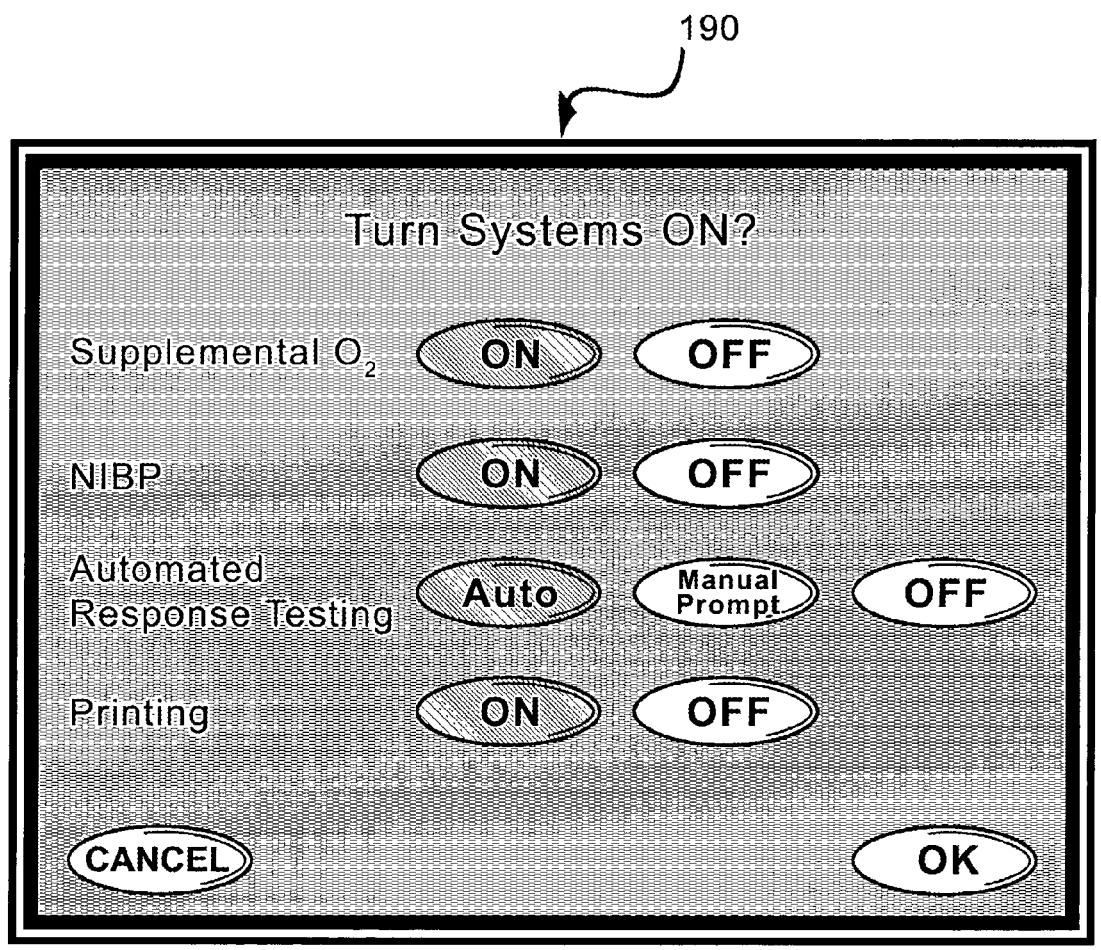
FIG. 28 shows an example display of a system initiation confirmation screen according to one embodiment of the present invention.

FIG. 28 shows an example of a system initiation confirmation screen 190. Upon the initiation of a first propofol administration to a new patient, UI 1 reminds user 3 to turn on monitors and subsystems at convenient points during the system start-up sequence thereby preventing the premature activation of subsystems which may result in distracting false-positive alarms (e.g., NIBP activation before the cuff is on the patient or ART activation before the patient is holding the hand piece), the dangerous activation of subsystems (e g , the administration of supplemental oxygen to a patient with hypoxic drive to breathe), and the inconvenient activation of subsystems (e.g., the initiation of printing before appropriate). These reminders may be presented to user 3 in the form of a system initiation confirmation screen 190 if during initiation delivery system 2 senses that one of the relevant monitors or subsystems is inactive. The default settings for each of the relevant monitors or subsystems may be active such that the user must proactively and consciously decide to turn them off prior to administration of propofol to the patient.

If user 3 attempts to administer sedatives such as propofol without first activating the NIBP monitor, delivery system 2 will automatically begin NIBP monitoring following confirmation by user 3 on a confirmation screen for Propofol administration.

Figure 29:
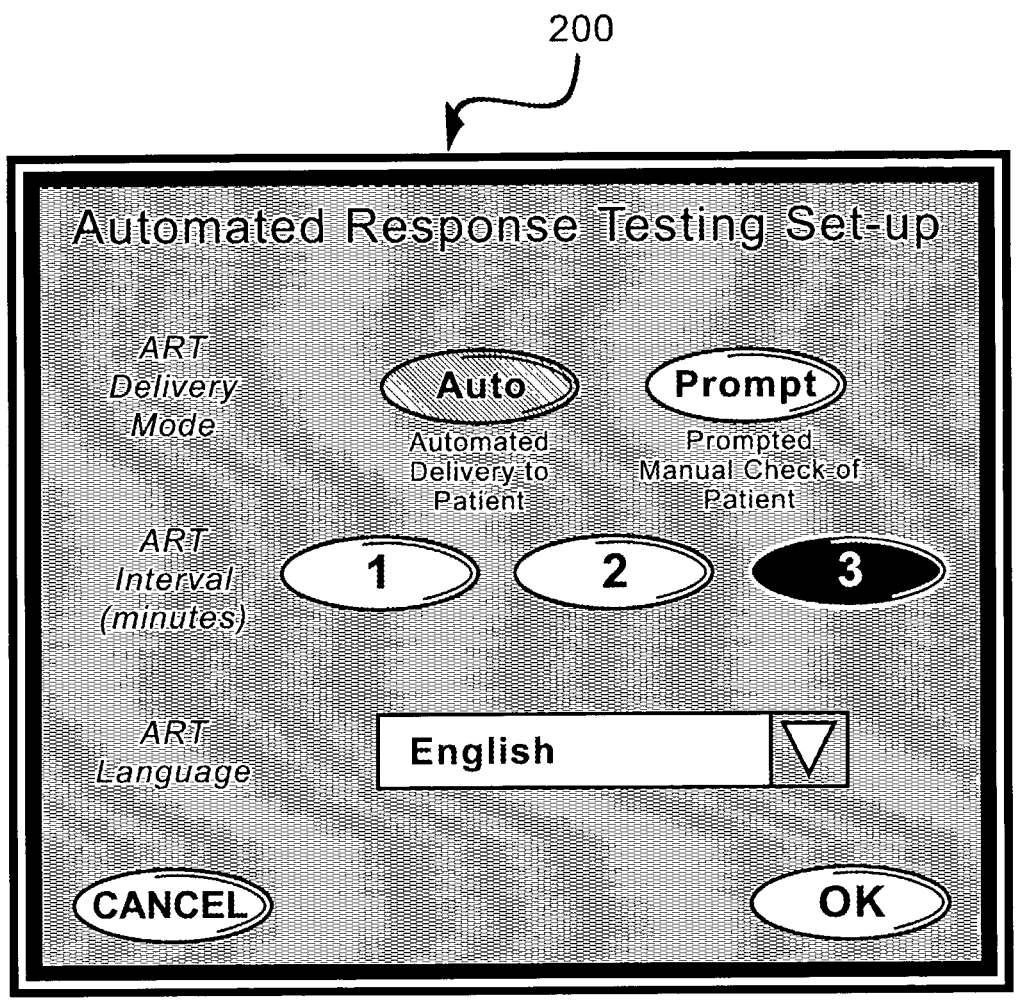
FIG. 29 shows an example of an ART set-up preferences display according to one embodiment of the present invention.

FIG. 29 shows an example of ART set-up preferences display 200. User 3 may alter preferences for certain monitors and subsystems by pressing the appropriate button on membrane keypad 34 (FIG. 3) to bring up a pop-up window. For example, a pop-up ART set-up preferences display 200 appears upon user 3 pressing the ART set-up button 62 and allows user 3 to change preferences related to ART delivery mode, interval, and language. User 3 may select whether to have delivery system 2 automatically administer responsiveness tests or to prompt user 3 to manually assess patient responsiveness. Under the interval preferences, user 3 may select how much time elapses between the responsiveness query cycles and under the language preferences, user 3 may select in what language delivery system 2 will prompt or query the patient.

Figure 30:
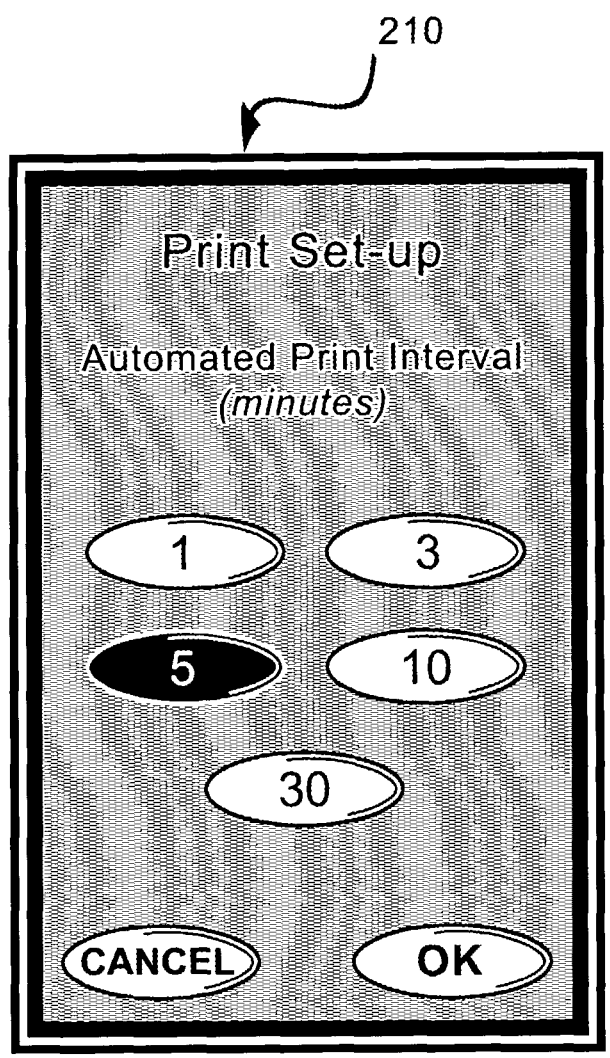
FIG. 30 shows an example of a print set-up preferences display according to one embodiment of the present invention.

FIG. 30 shows an example of print set-up preferences display 210 may be presented by UI 1 to allow user 3 to select how often an automated printout of key patient parameters will be produced by delivery system 2. Automated printing may be selected or de-selected via a Print on/off button 56c (FIG. 3) or via the system initiation confirmation screen.

Figure 31:
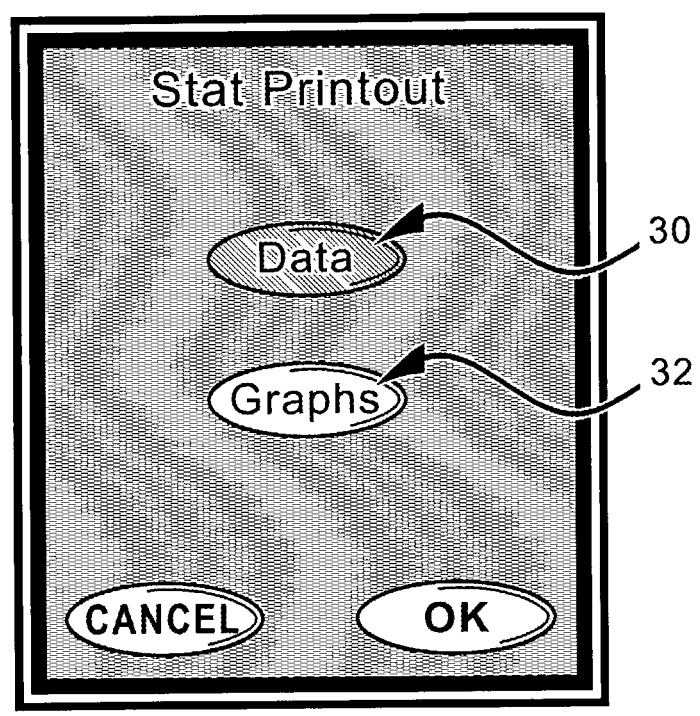
FIG. 31 shows an example display of a stat printout screen according to one embodiment of the present invention.

FIG. 31 shows an example display of the stat printout screen. From this screen, user 3 may select the button 30 to print textual and/or numerical data or the button 32 to print graphical waveforms. The print function of UI 1 is aimed at reducing another time and labor intensive aspect, namely keeping a written record of the physiological parameters of the patient and of clinical interventions such as drug infusion as well as the time at which these events occur. It takes time and labor to read the parameters displayed by stand-alone monitors and transcribe them manually to a medical record. Sometimes, the clinician is too busy to maintain the record as interventions are occurring, especially in emergencies when accurate record keeping is most important, and has to attempt to reconstruct what has occurred, after the fact, relying on memory that may be fallible. UI 1 is tightly integrated with the physiological monitors, drug delivery system 2 and the printer such that much of the time and labor required to maintain an accurate medical record is reduced via semi-automation.

Figure 32:
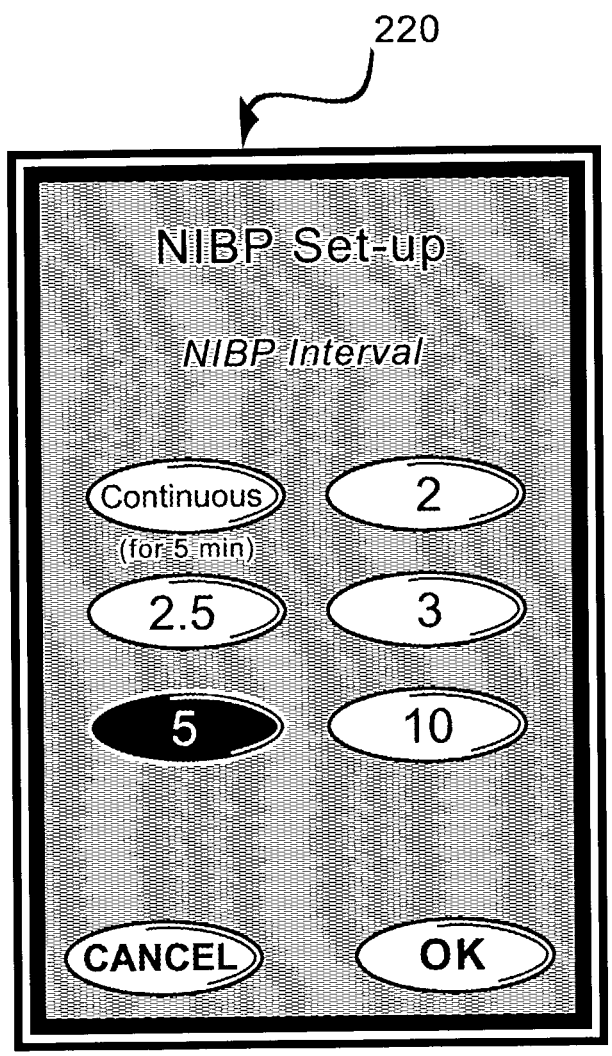
FIG. 32 shows an example of an NIBP set-up preferences display according to one embodiment of the present invention.

FIG. 32 shows an example of NIBP set-up preferences display 220 which may be presented by delivery system 2 to allow user 3 to select how often NIBP measurements are made by delivery system 2. The interval between measurements may be set to continuous to cause delivery system 2 to automatically take a new measurement immediately after a previous measurement. Delivery system 2 may also erase outdated NIBP data from the UI display after a set amount of time.

Figure 33:
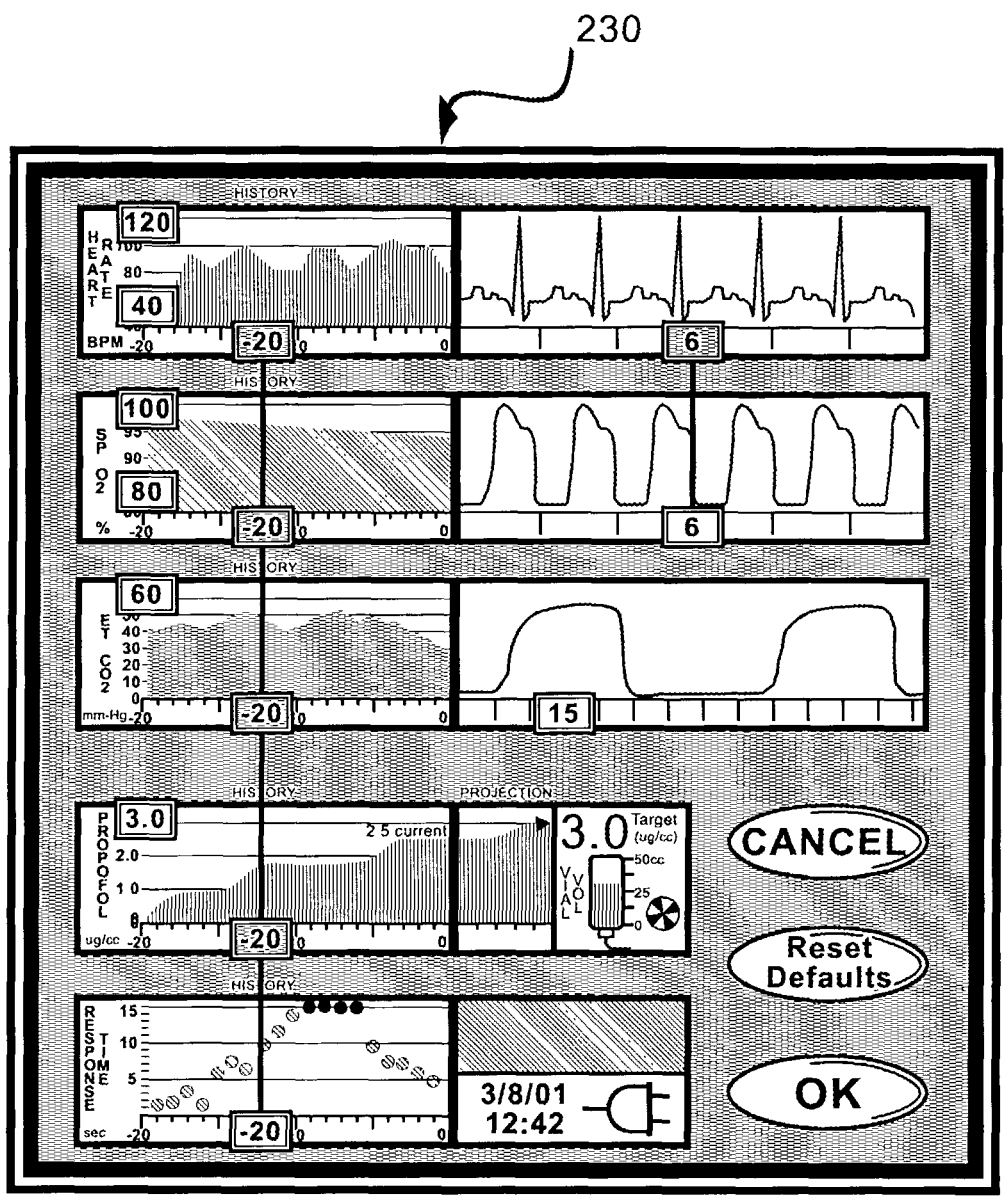
FIG. 33 shows an example of a scales set-up preferences display according to one embodiment of the present invention.

FIG. 33 shows an example of scales set-up preferences display 230 may be presented by delivery system 2 to allow user 3 to select the scale range for each modifiable scale on charts and graphs of other displays. The corresponding change to the scale and the current data may be shown on primary monitoring display 70 (FIG. 5). Each scale may be changed to a value within the limits provided with the system software. If user 3 selects a value outside of these limits, a scale limit error message will be displayed. To ensure proper resolution of data displayed, maximum scale values may need to be at least a certain number of units greater than the minimum scale values. Delivery system 2 may automatically adjust the scales to achieve the variation. This number of units varies depending upon the patient parameter and is included in the system software. An appropriate error message may be displayed to the user if he selects minimum and maximum scale values that exceed preset ranges for each parameter.

Figure 34:
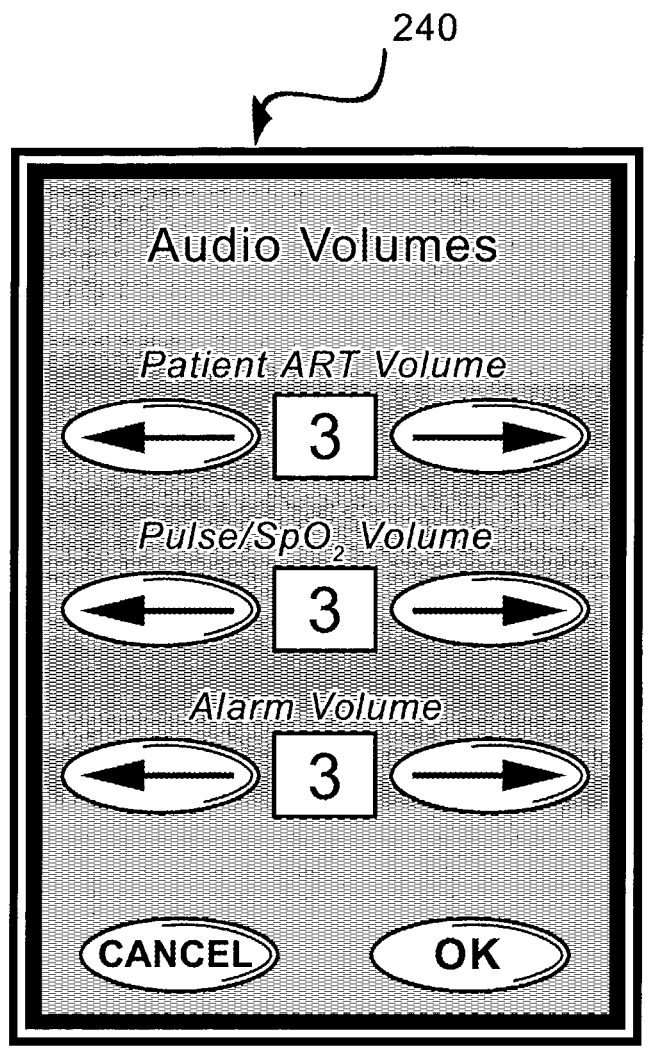
FIG. 34 shows an example of an audio volume set-up display according to one embodiment of the present invention.

FIG. 34 shows an example of audio volume set-up display 240 which may also be provided by UI 1 to allow user 3 to select the volume of audible output, such as for example, each of the ART audio presentation to the patient, the volume of the tones representing alarms and advisories, and the volume of the pulse/$SpO_2$ tone. Only the volume of the pulse/$SpO_2$ tone may be set to zero at this preference screen.

A system information display may also be provided by UI 1 upon pressing the system info button 43 on membrane keypad 34 (FIG. 3) to allow user 3 to alter any one or more of date, time, language presented on the system console, and brightness controls for the console display screen. Delivery system 2 may be set up so that changes to the console language may be made at the same time as the language used for the ART presentation to the patient.

Figure 35:
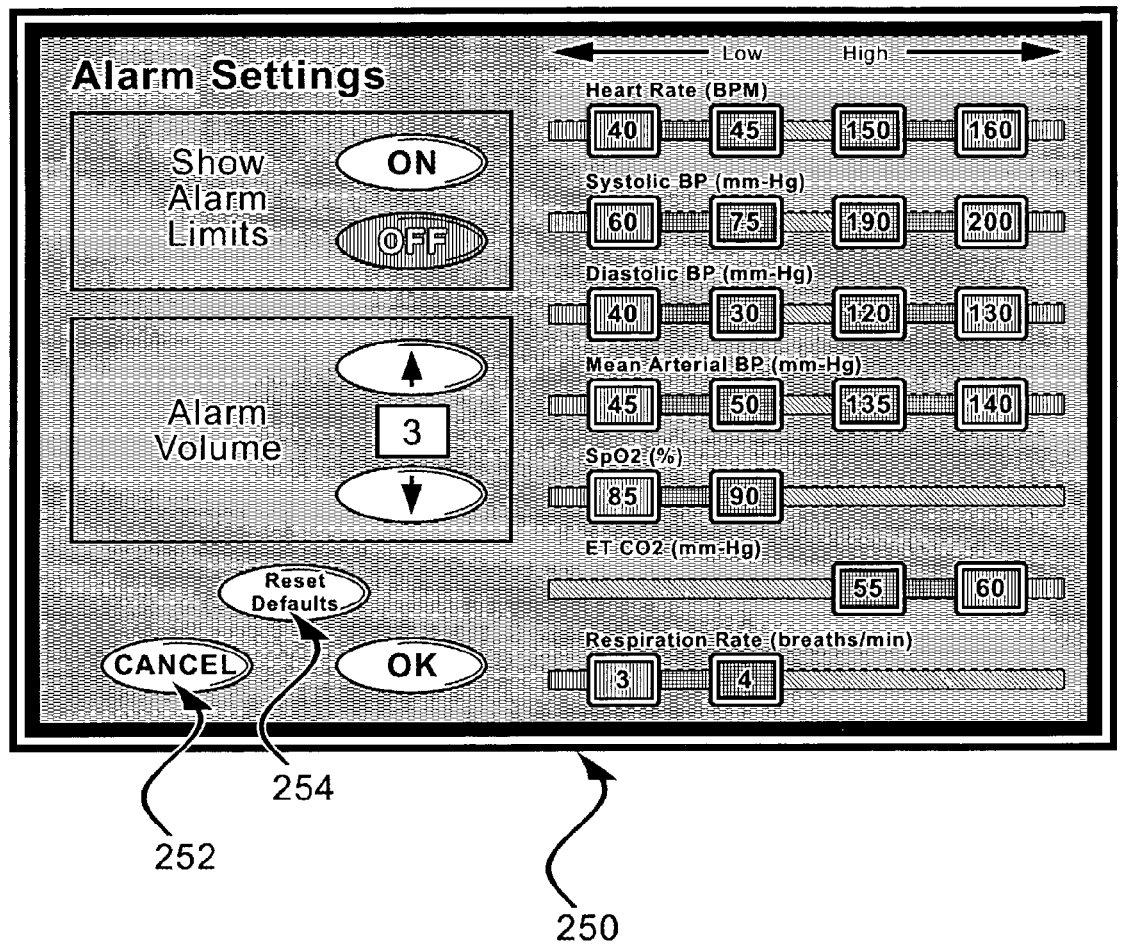
FIG. 35 shows an example of an alarm settings display according to one embodiment of the present invention.

FIG. 35 shows an example of alarm settings display 250 which may be presented as a pop-up window over primary monitoring display 70 (FIG. 5) upon user 3 pressing alarm settings button 45 on the membrane keypad 34 (FIG. 3). The software contains default limits for each alarm, but a user has some latitude within the system to change the limits. New values for each alarm limit (e.g., high warning, high caution, low caution, low warning) may be entered by user 3 by his touching the corresponding text entry box and inputting the new values using keypad 36 (FIG. 3). The entered values can be negated by touching cancel button 252, which will remove alarm settings display 250 and return primary monitoring display 70 to the front with no changes being made. Touching reset defaults button 254 will change all alarm limit values to their default values.

Figure 36:
FIG. 36 shows an example display of an alarm limit error message according to one embodiment of the present invention.

FIG. 36 shows an example of alarm limit error message 260. Caution and warning alarm limits for each physiological parameter of consequence are stored in a safety data set If user 3 enters an alarm limit that is outside the range limit stored in the safety data set for that parameter, alarm limit error message 260 will be displayed to user 3 to prompt him to enter a new alarm limit.

If the value user 3 enters in the text entry box for a high alarm limit is less than the value for the low alarm limit (warning or caution) for a particular physiological parameter, then UI 1 will present an appropriate error message to user 3. If the value user 3 enters in the text entry box for a low alarm limit is greater than the value for the high alarm limit (warning or caution) for a particular physiological parameter, then an appropriate error message will be presented to user 3.

If the value user 3 enters for a high warning alarm limit is less than the value for the high caution alarm limit, then the high caution alarm limit will be reset to a level, for example one unit, below the high warning alarm limit. If the value user 3 enters for a high caution alarm limit is greater than the value for the high warning alarm limit, the high warning alarm limit will be reset to a level, for example one unit, above the high caution alarm limit.

If the value user 3 enters for a low warning alarm limit is greater than the value entered for the corresponding yellow caution low alarm limit, the yellow caution low alarm limit will be reset to a level, for example one unit, above the red warning low alarm limit. If the entered value for a yellow caution low alarm limit is less than the value for the red warning low alarm limit, the red warning low alarm limit will be reset to a level, for example one unit, below the yellow caution low alarm limit.

User 3 may be given a choice of whether to display the current alarm limits on primary monitoring display 70. A button to show the alarm limits may be displayed on alarm settings display 250 (FIG. 35). When the button is switched on, the alarm limits for most alarmed parameters will be displayed in their respective parameter data boxes 82 on the primary monitoring display 70 as described above with respect to FIG. 5.

The volume of the audible alarm signals may also be controlled from alarm settings display 250 via up and down volume adjustment buttons. The alarm volume may not be reduced to zero by using the down volume adjustment button. Upon user 3 changing an alarm volume adjustment, the new volume level will be presented to user 3 by playing a short sound at the new volume.

Figure 37:
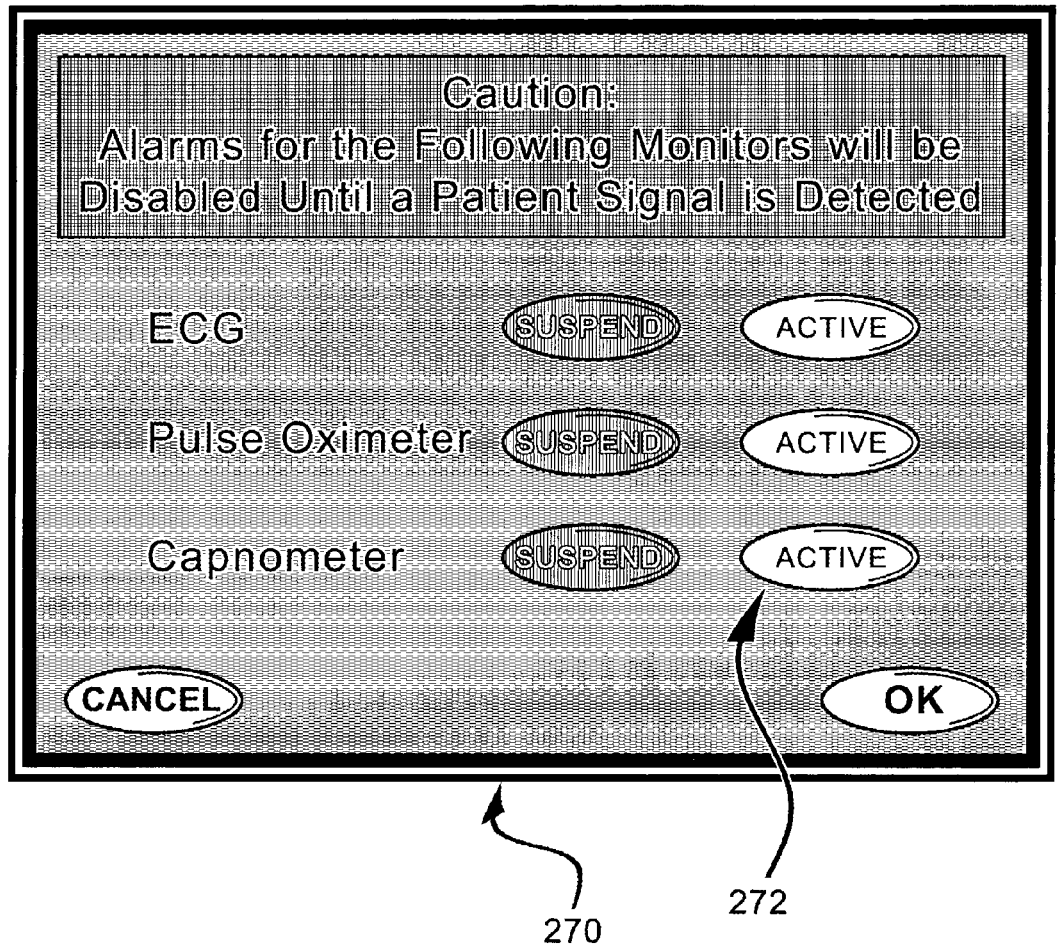
FIG. 37 shows an example of a suspend alarms confirmation display according to one embodiment of the present invention.

FIG. 37 shows an example of suspend alarms confirmation display 270 which may be a pop-up window which can be brought up over the primary monitoring display 70 (FIG. 5) by pressing a suspend alarms button 11 on the membrane keypad 34 (FIG. 3). The parameter alarms and advisories associated with certain patient monitors may be set to be suspended by the system for the duration of time that there is no patient signal detected. This option may be selected by user 3 for each suspendable alarm by corresponding touch buttons on suspend alarms confirmation display 270 or after pressing suspend alarms button 11. After a monitor has been disabled by the suspend function, the parameter may alarm and advisories associated with that monitor may be automatically reactivated if a patient signal is detected on the associated parameter sensor. The alarms and advisories may also be reactivated manually by user 3 by his touching the corresponding active button 272 on Suspend alarms confirmation display 270.

If an ECG signal is not available, the source of the heart rate reading (and thereby the input to the heart rate alarm algorithm) displayed to the user will switch from the ECG monitor to the pulse oximeter, if available. Likewise, if a pulse oximetry signal is not available, the source of the heart rate reading (and alarm input) will switch to the ECG monitor, if available . For any parameter that is not available due to its monitor e g, NIBP, CO2, SpO2 and ECG monitors, being suspended, non-functional, turned off or absent: a designation of no reading ("- - - " for example) will be shown in the associated parameter box 82 on primary monitoring display 70 (FIG. 5). Removing the display of a parameter derived from a monitor that is suspended, non-functional, turned off or absent prevents the outdated parameter, if displayed, from being misinterpreted as recent data indicative of the current physiological status of the patient and lulling the user into thinking that the corresponding monitor is turned on and functional as described previously for the NIBP monitor. However, the lack of data from a suspended monitor may continue to be displayed on the history box to let the user know when the monitor was suspended or turned off Also, if a device is suspended, the label "SUSPENDED" will be displayed in the associated real-time Data box 72 on primary monitoring display 70, if available.

As a part of the start-up process of delivery system 2, user 3 may be presented with an introduction screen, then the patient information display, then the patient information confirmation display, and finally primary monitoring display 70 (FIG. 5). Following the system start-up sequence the selection of the display screens is at the user's control.

A new procedure may be initiated by user 3 by pressing new case button 15 on membrane keypad 34 (FIG. 3). If delivery system 2 detects a new cassette at any time after propofol has been initiated in the procedure, UI 1 will remind user 3 to properly terminate a previous procedure (by pressing end case key 19) prior to starting a new one, if the cassette has been in use for less than 6 hours. If the cassette has been in use for 6 hours, UI 1 may prompt user 3 to change the cassette and confirm if the patient is still the same patient and that the case has not ended. In response to user 3 selecting that a procedure has ended, delivery system 2 causes all previous patient data to be cleared from its memory following a final print-out of case information (if printing is enabled), and it resets the modifiable system settings to their default values. Delivery system 2 then repeats the system startup process by presenting patient information display 110 (described above with respect to FIG. 20).

Delivery system 2 registers an end-of-case whenever the user presses end case button 19 or on/off button 38 on membrane keypad 34 (FIG. 3) while delivery system 2 is active. Upon registering an end-of-case, delivery system 2 confirms the user's intent to shut down by presenting him with a shut down confirmation display. User 3 must then touch a button to affirm the end-of-case causing delivery system 2 to discontinue propofol administration, cease ART and NIBP administration, and print a final report of patient data (if printing is enabled).

Delivery system 2 also registers an end-of-case when no data is detected from all of the active health monitors (ECG, pulse oximeter, and capnometer). Upon such an event, an end-of-case confirmation display is presented to user 3 which gives him the option of shutting down delivery system 2, or suspending all alarms for a period of time, following which only a fixed number (e.g. 5) of additional alarm suspensions are allowed before delivery system 2 thereafter considers the cassette as invalid. If data is still not detected after the suspension period, delivery system 2 will automatically go into a shut-down mode.

A total maximum amount of time (e.g., six hours) of vial usage will be allowed by delivery system 2 in any particular procedure Upon elapse of this amount of time, an advisory alarm will be generated indicating that the vial time limit has been exceeded. A similar advisory alarm will be generated when the maximum amount of time of cassette usage has been exceeded.

When AC power is lost, a system advisory (described above) is provided to user 3. UI 1 may also alert user 3 with an appropriate message when the remaining battery power falls below a particular level (e.g., 6 minutes of operation remaining). Delivery system 2 may also be set up to stop propofol administration to a patient and provide user 3 with an appropriate message whenever the remaining battery power falls below a certain level (e.g., 5 minutes of operation remaining). Delivery system 2 will thus continue to operate for a sufficient amount of time to safely see the patient through recovery. In the event that the electronic controller of delivery system 2 fails, an audible alarm sounds and the system fault LED 64 will light (FIG. 3). Delivery system 2 fails to a safe condition, i.e., propofol flow is off, no new NIBP measurements are initiated, any ongoing NIBP measurement is aborted and the NIBP cuff is depressurized, and supplemental oxygen is at a steady flow (if oxygen was being administered at the time of the failure). Supplemental $O_2$ may then be administered for a limited amount of time and then discontinued.

If after a given parameter monitor has been initially connected to the patient and if more than two minutes pass with no data from that monitor (unless it has been suspended by the user as described above), UI 1 will display a monitor error display to user 3. From this display, user 3 has the option of selecting for no more alarms or advisories to be presented regarding that parameter, i.e., the alarms will be suspended for that parameter as long as no patient data is detected from the monitor. An appropriate message (e.g., a set of dashes " - - - ") is then displayed in the corresponding parameter box on primary monitoring display 70 to indicate that the parameter is not being monitored by the system and a message is also displayed in the associated real-time data box 72.

The invention claimed is:

1. An improved system for enabling a non-anesthestist practioner to provide safe and effective sedation with the drug propofol to a patient undergoing a medical procedure performed by a procedural physician without general anesthesia, the system comprising:
    one or more patient health monitor devices adapted so as to receive a signal reflecting at least one physiological condition of said patient;
    a drug delivery controller for administering the drug propofol to said patient;
    a user interface sub-system for receiving user input from said non-anesthetist relating to patient weight, and for providing system information regarding the supply of propofol, information regarding the at least one physiological condition, and information that warns said non-anesthetist said user via said user interface if said administration of propofol has placed the patient in one of the following conditions: general anesthesia, low $SpO_2$, low respiratory rate, respiratory obstruction, loss of responsiveness, bradycardia, tachycardia, excessively high or low arterial blood pressures, and
    an electronic controller having a data set reflecting safe and/or unsafe parameters of the al least one physiological condition operably connected to the one or more patient health monitor devices, the drug delivery controller, and the user interface sub-system; wherein said electronic controller receives said signal reflecting at least one physiological condition and said user input, and in response manages the application of propofol.

2. The system according to claim 1, wherein the user interface sub-system comprises:
    at least one of a touch screen or multi-layer display for displaying and for receiving user input regarding the system, the administration of sedation and analgesia, and the at least one physiological condition; and
    a separate set of hard buttons for interacting with the system independently of the touch screen or multi-layer display.

3. The system according to claim 1, wherein the user interface sub-system comprises at least one device for monitoring the system information, the information regarding the administration of propofol, and the information regarding the at least one physiological condition in relation to the parameters and at least one device for allowing the user to control the drug delivery controller and the electronic controller.

4. The system according to claim 3, wherein the at least one physiological condition is selected from the group consisting of ECG, heart rate, blood pressures, Sp02, respiratory rate, ETC02, and patient responsiveness.

5. The system according to claim 3, wherein data from the one or more patient health monitor devices is grouped in geographical areas when displayed on the single screen or multi-layer display, and wherein each geographical area includes data relevant to a patient physiological condition.

6. The system according to claim 5, wherein the data from the one or more patient health monitor devices is grouped in a cardiovascular data geographical area, an oxygenation data geographical area, and a ventilation data geographical area.

7. The system according to claim 6, wherein the oxygenation data geographical area is adjacent to the cardiovascular data geographical area.

8. The system according to claim 6, wherein the oxygenation data geographical area is adjacent to the ventilation data geographical area.

9. The system according to claim 3, wherein the information regarding the administration of propofol comprises information regarding patient drug levels based on pharmacokinetic calculations, and wherein the information regarding the patient drug levels and the information regarding the at least one physiological condition are displayed on the single screen or multi-layer display in positions that facilitate the user in cross-correlating the information regarding the patient drug levels and the information regarding the at least one physiological condition.

10. The system according to claim 9, wherein the single screen or multi-layer display comprises a dedicated portion for displaying information regarding patient state alarms and advisories and system state alarms and advisories.

11. The system according to claim 10, wherein information regarding current alarms and advisories is displayed on the single screen or multi-layer display in positions determined by a priority of the alarms and advisories.

12. The system according to claim 10, wherein the user interface sub-system relays audible indicators to the user that are redundantly indicative of the information regarding the patient state alarms and advisories and system state alarms and advisories displayed to the user.

13. The system according to claim 12, wherein the redundant audible indicators are mutable by the user via the user interface sub-system.

14. The system according to claim 13, wherein a muted redundant audible indicator will remain muted for a pre-set period of time, and wherein the amount of mute time remaining is displayed to the user.

15. The system according to claim 10, wherein information regarding current alarms and advisories is color coded wherein the colors displayed indicate the priority of the alarms and advisories.

16. The system according to claim 1, wherein the system information, the information regarding the administration of propofol, and the information regarding the at least one physiological condition are consistently updated throughout a procedure that is accompanied by the administration of propofol.

17. The system according to claim 1, wherein the system information, the information regarding the administration of propofol, and the information regarding the at least one physiological condition comprise real-time data and historical data.

18. The system according to claim 17, wherein a portion of the real-time data is displayed to the user both as a numerical value and as a graphical waveform.

19. The system according to claim 1, wherein the system information, the information regarding the administration of propofol, and the information regarding the at least one physiological condition are displayed to the user according to a color coded display schema.

20. The system according to claim 1, wherein the system information, the information regarding the administration of propofol and the information regarding the at least one physiological condition comprise information regarding patient state alarms and advisories and system state alarms and advisories.

21. The system according to claim 1, wherein said non-anesthetist is provided with a warning if the user input exceeds the maximum recommended rate for dose, infusion rate and/or effect site concentration, 22. The system according to claim 1, wherein the user interface sub-system displays data from the one or more patient health monitor devices and the information regarding the administration of propofol at a single screen or multi-layer display.

23. An improved method for the safe and effective administration of sedation drugs to a patient undergoing medical and/or surgical procedures by a non-anesthetist without general anesthesia, said method comprising the steps of:
  a) connecting to a patient a drug delivery device having a drug delivery controller supplying one or more of said drugs, said drug delivery controller being coupled to an electronic controller which controls the delivery of the drugs to the patient;
  b) attaching one or more patient health monitor devices to said patient to reflect a value of at least one physiological condition of said patient for input to said electronic controller;
  c) said electronic controller accessing parameters, said parameters including default settings for delivery of drugs to said patient and predetermined values of said monitored physiological condition correlating to safe and effective sedation;
  d) said electronic controller comparing said values generated by said patient health monitor devices with said parameters;
  e) said electronic controller causing said drug delivery device to modify said desired supply rate of the drugs as necessary in response to said comparing in order to maintain said patient safely within said normal levels of desired sedation during said procedure; and
  f) a user interface for permitting input of patient data including patient weight, and for providing information regarding the at least one physiological condition of a patient, and information regarding the delivery of one or more of said drugs, and for warning the non-anesthestist user if the user input and/or the physiological condition of the patient is unsafe.

24. The method of claim 23, wherein the step of attaching one or more patient health monitor devices to a patient comprises attaching patient health monitor devices generating values reflecting patient responsiveness, respiratory effort, and/or oxygenation.

25. The method of claim 24 further comprising the step of presenting the user with a list of ramifications of the user input.

26. The method of claim 23, wherein the step of providing to the user information regarding the at least one physiological condition of a patient and regarding the step of delivery of one or more drugs comprises displaying the information at a single screen or multi-layer display.

27. The method of claim 26, wherein the step of displaying the information at a single screen or multi-layer display comprises the step of grouping the information geographically in a way that facilitates the user to cross-correlate different aspects of the information.

28. The method of claim 26, wherein the step of displaying the information at a single screen or multi-layer display comprises the step of graphically color coding the information in a way that allows the user to quickly assess the relevance of the information to the safe administration of sedation and analgesia.

29. The method of claim 26, wherein the step of displaying the information at a single screen or multi-layer display comprises the step of segregating a portion of the screen or multi-layer display for the dedicated display of system state alarms and advisories and patient state alarms and advisories.

30. The method of claim 29, wherein the step of segregating a portion of the screen or multi-layer display for the dedicated display of system state alarms and advisories and patient state alarms and advisories comprises the step of graphically color coding the segregated portion and display of the system state alarms and advisories and patient state alarms and advisories in a way that allows the user to quickly assess the priority and importance of the system state alarms and advisories and patient state alarms and advisories.

31. The method of claim 23, wherein the step of relaying to the user information regarding the at least one physiological condition of a patient and regarding the step of delivering one or more drugs comprises playing an audible indicator to the user.

32. The method of claim 23 further comprising the step of said user interface prompting the user to confirm changes made to settings of the drug delivery device, or the electronic controller.

33. The method of claim 23 further comprising the step of said user interface continuously notifying the user of changes made to the default settings of the drug delivery device by the electronic controller.

34. The method of claim 23 further comprising the step of reminding the user to ensure that requisite predecessor conditions to the safe administration of sedation are satisfied prior to the step of said electronic controller causing said controllable drug delivery device to modify said desired supply rate of the drugs as necessary.

35. The method of claim 23, wherein the step of receiving input from the user of the drug delivery device, or the electronic controller comprises the steps of receiving input from the user via a touch screen or multi-layer display and receiving input regarding the activation of functionalities of the drug delivery device, or the electronic controller from the user via a separate set of hard keys.

36. The method of claim 23 wherein the step of receiving input from the user of the drug delivery device, or the electronic controller further comprises the step of checking the user input versus known data and/or weight nomograms.

\* \* \* \* \*